US008110367B2

(12) United States Patent
Riser et al.

(10) Patent No.: US 8,110,367 B2
(45) Date of Patent: Feb. 7, 2012

(54) METHODS FOR DIAGNOSING RENAL DISORDERS

(75) Inventors: Bruce L. Riser, Marshall, MI (US); Mark DeNichilo, Grange (AU)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 12/221,371

(22) Filed: Aug. 1, 2008

(65) Prior Publication Data

US 2009/0017559 A1  Jan. 15, 2009

Related U.S. Application Data

(63) Continuation of application No. 10/687,479, filed on Oct. 16, 2003, now abandoned, which is a continuation of application No. 09/392,024, filed on Sep. 8, 1999, now abandoned.

(60) Provisional application No. 60/112,855, filed on Dec. 16, 1998, provisional application No. 60/099,471, filed on Sep. 8, 1998.

(51) Int. Cl.
*G01N 33/53* (2006.01)
(52) U.S. Cl. ........................................................ 435/7.1
(58) Field of Classification Search ........................ None
See application file for complete search history.

(56) References Cited

U.S. PATENT DOCUMENTS

| 4,281,061 | A  | 7/1981 | Zuk et al. |
| 5,408,040 | A  | 4/1995 | Grotendorst et al. |
| 5,753,517 | A  | 5/1998 | Brooks et al. |
| 6,232,064 | B1 | 5/2001 | Grotendorst et al. |

FOREIGN PATENT DOCUMENTS

| WO | WO 96/38172    | 12/1996 |
| WO | WO-96/38172 A1 | 12/1996 |
| WO | WO 99/33878    | 7/1999  |
| WO | WO-99/33878 A1 | 7/1999  |

OTHER PUBLICATIONS

Yoshioka et al. 'In situ expression of cytokines in IgA nephritis.' Kidney International. 44:825-833, 1993.*
Pepe et l. 'Pivotal evaluation of the accuracy of a biomarker used for classification or prediction:standards for study design.' JNCI. 100(20):1432-1438, 2010.*
Yue et al. 'Urinary connective tissue growth factor is a biomarker in a rat model of chronic nephopathy.' Transplantation Proceedings 42:1875-1880, 2010.*
Kazin et al. 'Renal proximal tubular dysfunction is a major determinant of urinary connective tissue growth factor excretion.' Am. J. physiol. Renal. Physiol. 298:F1457-F1464, 2010.*
Andersen, A. R., et al., "Diabetic Nephropathy in Type 1 (Insulin-Dependent) Diabetes: An Epidemiological Study," Diabetologia (1983) vol. 25, pp. 496-501.
Anderson, Sharon, et al., "Control of Glomerular Hypertension Limits Glomerular Injury in Rats With Reduced Renal Mass," J. Clin. Invest. (1985) vol. 76, pp. 612-619.
Bohle, A., et al., "The Pathogenesis of Renal Failure," Path. Res. Pract. (1989) vol. 185, pp. 421-440.
Bojestig, Mats, et al., "Glycemic Control and Prognosis in Type 1 Diabetic Patients With Microalbuminuria," Diabetes Care (1996) vol. 19, No. 4, pp. 313-317.
Border, Wayne A., et al., "Supression of Experimental Glomerulonephritis by Antiserum Against Transforming Growth Factor β1," Nature (1990) vol. 346, pp. 371-374.
Border, Wayne A., et al., "Cytokines in Kidney Disease: The Role of Transforming Growth Factor β" Am. J. Kidney Dis. (1993) vol. 22, pp. 105-113.
Bradham, Douglas M., et al., "Connective Tissue Growth Factor: A Cysteine-Rich Mitogen Secreted by Human Vascular Endothelial Cells is SRC-Induced Immediate Early Gene Product CEF-10," J. Cell Biol. (1991) vol. 114, No. 6, pp. 1285-1294.
Brigstock, David R., et al., "Purification and Characterization of Novel Heparin-Binding Growth Factors in Uterine Secretory Fluids," J. Biol. Chem. (1997) vol. 272, No. 32, pp. 20275-20282.
Bruneval, Patrick, et al., "Glomerular Matrix Proteins in Nodular Glomerulosclerosis in Association With Light Chain Depostion Disease and Diabetes Mellitus," Human Pathol. (1985) vol. 16, pp. 477-484.
Clarkson, Michael R., et al., "Connective Tissue Growth Factor: A Potential Stimulus for Glomerulosclerosis and Tubulointerstitial Fibrosis in Progressive Renal Disease," Cur. Opin. Nephrol. Hypertens. (1999) vol. 8, pp. 543-548.
Cortes, Pedro, et al., "Role of Glomerular Mechanical Strain in the Pathogenesis of Diabetic Nephropathy," Kidney Int. (1997) vol. 51, pp. 57-68.
Duncan, Matthew R., et al., "Connective Tissue Growth Factor Mediates Transforming Growth Factor β-Induced Collagen Synthesis: Down-Regulation by cAMP," FASEB J. (1999) vol. 13, pp. 1774-1786.
Franklin, T.J., "Therapeutic Approaches to Organ Fibrosis," Int. J. Biochem. Cell Biol. (1997) vol. 29, No. 1, pp. 79-89.
Frazier, K.S., et al., "Connective Tissue Growth Factor Expression in the Rat Remnant Kidney Model and Association With Tubular Epithelial Cells Undergoing Transdifferentiation," Vet. Pathol. (2000) vol. 37, pp. 328-335.
Goldschmeding, Roel, et al., "Connective Tissue Growth Factor: Just Another Factor in Renal Fibrosis?," Nephrol. Dial. Transplant. (2000) vol. 15, pp. 296-299.
Gupta, Sunil, et al., "Connective Tissue Growth Factor: Potential Role in Glomerulosclerosis and Tubulointerstitial Fibrosis," Kidney Int. (2000) vol. 58, pp. 1389-1399.
Gygi, Steven P., et al., "Correlation Between Protein and mRNA Abundance in Yeast," Mol. Cell Biol. (1999) vol. 19, No. 3, pp. 1720-1730.
Haberstroh, Uwe, et al., "TGF-β Stimulates Rat Mesangial Cell Proliferation in Culture: Role of PDGF β-Receptor Expression," Am. J. Physiol. (1993) vol. 264, pp. F199-F205.

(Continued)

*Primary Examiner* — Nora Rooney
(74) *Attorney, Agent, or Firm* — Leanne C. Price, Esq.; Paul E. Borchardt

(57) ABSTRACT

The present invention relates to methods for diagnosing the presence and progress of pathologies characterized by an accumulation of the extracellular matrix components by measuring the level of Connective Tissue Growth Factor (CTGF) in a sample. The method of the present invention is directed to diagnosing kidney fibrosis and associated renal disorders, in particular, complications associated with diabetes, hyperglycemia, and hypertension.

5 Claims, 12 Drawing Sheets

OTHER PUBLICATIONS

Hammes, Mary S., et al., "Calcium Oxalate Monohydrate Crystals Stimulate Gene Expression in Renal Epithelial Cells," Kidney Int. (1995) vol. 48, pp. 501-509.
Haneda, M., et al., "Glucose Enhances Type IV Collagen Production in Cultured Rat Glomerular Mesangial Cells," Diabetologia (1991) vol. 34, pp. 198-200.
Hostetter, Thomas H., et al., "Glomerular Hemodynamics in Experimental Diabetes Mellitus," Kidney Int. (1981) vol. 19, pp. 410-415.
Hsueh, Willa A., et al., "Hypertension, the Endothelial Cell, and the Vascular Complications of Diabetes Mellitus," Hypertension (1992) vol. 20, No. 2, pp. 253-263.
Igarashi, Atsiyuki, et al., "Significant Correlation Between Connective Tissue Growth Factor Gene Expression and Gene Sclerosis in Tissue Sections From Patients With Systemic Sclerosis," J. Invest. Dermatology (1995) vol. 105, pp. 280-284.
Igarashi, Atsiyuki, et al., "Connective Tissue Growth Factor Gene Expression in Tissue Sections From Localized Scleroderma Keloid, and Other Fibrotic Skin Disorders," J. Invest. Dermatology (1996) vol. 106, pp. 729-733.
Ito, Yasuhiko, et al., "CTGF (Connective Tissue Growth Factor) in Human Glomerular and Tubulointerstitial Fibrosis," J. Am. Soc. Nephrol. (1997) vol. 8, pp. A2502.
Ito, Yasuhiko, et al., "Expression of Connective Tissue Growth Factor in Human Renal Fibrosis," Kidney Int. (1998) vol. 53, pp. 853-861.
Lewis, Edmund J., et al., "The Effect of Angiotensin-Converting-Enzyme Inhibition on Diabetic Nephropathy," (1993) N. Eng. J. Med., vol. 329, pp. 1456-1462.
Mauer, S. Michael, et al., "Structural-Functional Relationships in Diabetic Nephropathy," J. Clin. Invest. (1984) vol. 74, pp. 1143-1155.
Mogensen, Carl E., et al., "Prevention of Diabetic Renal Disease With Special Reference to Microalbuminaria," Lancet (1995) vol. 346, pp. 1080-1084.
Nahman, N. Stanley, et al., "Effects of High Glucose on Cellular Proliferation and Fibronectin Production by Cultured Human Mesangial Cells," Kidney Int. (1992) vol. 41, pp. 396-402.
Nguyen, Tri Q., et al., "Urinary Connective Tissue Growth Factor Excretion Correlates With Clinical Markers of Renal Disease in a Large Population of Type 1 Diabetic Patients With Diabetic Nephropathy," Diabetes Care (2006) vol. 29, No. 1, pp. 83-88.
Oemar, Barry S., et al., "Human Connective Tissue Growth Factor is Expressed in Advanced Atherosclerotic Lesions," Circulation (1997) vol. 95, pp. 831-839.
Parving, Hans-Henrik, et al., "Prognosis in Diabetic Nephropathy," Brit. Med. J. (1989) vol. 299, pp. 230-233.
Pawar, Shashi, et al., "Differential Gene Expression in Migrating Renal Epithelial Cells After Wounding," J. Cell. Physiol. (1995) vol. 165, pp. 556-565.
Riser, Bruce L., et al., "Intraglomerular Pressure and Mesangial Stretching Stimulate Extracellular Matrix Formation in the Rat," J. Clin. Invest. (1992) vol. 90, pp. 1932-1943.
Riser, Bruce L., et al., "Cyclic Stretching Force Selectively Up-Regulates Transforming Growth Factor-β Isoforms in Cultured Rat Mesangial Cells," Am. J. Path. (1996) vol. 148, No. 6, pp. 1915-1923.
Riser, Bruce L., et al., "Connective Tissue Growth Factor (CTGF) as a Determinant of Extracellular Matrix (ECM) Deposition in Diabetic Glomerulosclerosis," J. Am. Soc. Nephrol. (1998) vol. 9, pp. A3269.
Riser, Bruce L., et al., "Mechanical Strain- and High Glucose-Induced Alterations in Mesangial Cell Collagen Metabolism: Role of TGF-β," J. Am. Soc. Nephrol. (1998) vol. 9, pp. 827-836.
Riser, Bruce L., et al., "TGF-β Receptor Expression and Binding in Rat Mesangial Cells: Modulation by Glucose and Cyclic Mechanical Strain," Kidney Int. (1999) vol. 56, pp. 428-439.
Riser, Bruce L., et al., "Regulation of Connective Tissue Growth Factor Activity in Cultured Rat Mesangial Cells and Its Expression in Experimental Diabetic Glomerulosclerosis ," J. Am. Soc. Nephrol. (2000) vol. 11, pp. 25-38.
Sharma, Kumar, et al., "The Transforming Growth Factor-β System and the Kidney," Seminars in Nephrology (1993) vol. 13, No. 1, pp. 116-128.
Sharma, Kumar, et al., "Neutralization of TGF-β by Anti-TGF-62 -0 Antibody Attenuates Kidney Hypertrophy and the Enhanced Extracellular Matrix Gene Expression in STZ-Induced Diabetic Mice," Diabetes (1996) vol. 45, pp. 522-530.
Stehouwer, C.D.A, et al., "Urinary Albumin Excretion, Cardiovascular Disease and Endothelial Dysfunction in Non-Insulin-Dependent Diabetes Mellitus," Lancet (1992) vol. 340, No. 8815, pp. 319-323.
The Diabetes Control and Complications Trial Research Group, "The Effect of Intensive Treatment of Diabetes on the Development and Progression of Long-Term Complications in Insulin-Dependent Diabetes Mellitus," N. Engl. J. Med. (1993) vol. 329, No. 14, pp. 977-986.
Tuttle, Katherine R. et al., "Effect of Strict Glycemic Control on RenalHemodynamic Response to Amino Acids and Renal Enlargemtn in Insulin-Dependent Diabetes Mellitus," N. Engl. J. Med. (1991) vol. 324, pp. 1626-1632.
Ziyadeh, Fuad N., et al., Stimulation of Collagen Gene Expression and Protein Synthesis in Murine Mesangial Cells by High Glucose is Mediated byAutocrine Activation of Transf.
Andersen et al. (1983) Diabetologia 25:496-501.
Anderson et al. (1985) J. Clin. Invest. 76:612-619.
Bohle et al. (1989) Path. Res. Pract. 185:421-440.
Bojestig et al. (1996) Diabetes Care 19:313-317.
Border et al. (1990) Nature 346:371-374.
Border et al. (1993) Am. J. Kidney Dis. 22:105-113.
Bradham et al. (1991) J. Cell Biology 114:1285-1294.
Brigstock et al. (1997) J. Biol. Chem. 272:20275-20282.
Bruneval et al. (1985) Human Pathol. 16:477-484.
Clarkson et al (1999) Cur. Opin. Nephrol. Hypertens. 8:543-548.
Cortes et al. (1997) Kidney Int. 51:57-68.
Duncan et al. (1999) FASEB J. 13:1774-1786.
Frazier et al. (2000) Vet. Pathol. 37:328-335.
Goldschmeding et al. (2000) Nephrol. Dial. Transplant. 15:296-299.
Gupta et al. (2000) Kidney Int. 58:1389-1399.
Haberstroh et al. (1993) Am. J. Physiol. 264:F199-F205.
Hammes et al. (1995) Kidney International 48:501-509.
Haneda et al. (1991) Diabetologia 34:198-200.
Hostetter et al. (1981) Kidney Int. 19:410-415.
Hsueh and Anderson (1992) Hypertension 20:253-263.
Igarashi et al. (1995) J. Invest. Dermatology 105:280-284.
Igarashi et al. (1996) J. Invest. Dermatology 106:729-733.
Ito et al. (1997) J. Am. Soc. Nephrol. 8:A2502.
Ito et al. (1998) Kidney International 53:853-861.
Lewis et al. (1993) N. Eng. J. Med., 329:1456-1462.
Mauer et al. (1984) J. Clin. Invest. 74:1143-1155.
Mogensen et al. (1995) Lancet 346:1080-1084.
Nahman et al. (1992) Kidney Int. 41:396-402.
Oemar et al. (1997) Circulation 95:831-839.
Parving and Hommel (1989) Brit. Med. J. 299:230-233.
Pawar et al. (1995) J. Cellular Physiology 165:556-565.
Riser et al. (1992) J. Clin. Invest. 90:1932-1943.
Riser et al. (1996) Am. J. Path. 148:1915-1923.
Riser et al (1998) J. Am. Soc. Nephrol. 9:A3269.
Riser et al. (1998) J. Am. Soc. Nephrol. 9:827-836.
Riser et al. (1999) Kidney Int. 56:428-439.
Riser et al (2000) J. Am. Soc. Nephrol. 11:25-38.
Sharma and Ziyadeh (1993) Seminars in Nephrology 13:116-128.
Sharma et al. (1996) Diabetes 45:522-530.
Stehouwer et al. (1992) Lancet 340:319-323.
The Diabetes Control and Complications Trial Research Group (1993) N. Engl. J. Med. 329:977-986.
Tuttle et al. (1991) N. Engl. J. Med. 324:1626-1632.
Ziyadeh et al. (1994) J. Clin Invest. 93:536-542.
Franklin (1997) Int. J. Biochem. Cell Biol. 29:79-89.
Andersen, S., et al., "Reduction of Urinary Connective Tissue Growth Factor by Losartan in Type 1 Patients With Diabetic Nephropathy," Kidney Int. (2005) Abstract of: 67(6):2325-2329.
Bollineni, J.S. and Reddi, A.S., "Transforming Growth Factor-Beta 1 Enhances Glomerular Collagen Synthesis in Diabetic Rats," Diabetes (1993) Abstract of: 42(11):1673-1677.
Gilbert, Richard E., et al., "Urinary Connective Tissue Growth Factor Excretion in Patients With Type 1 Diabetes and Nephropathy," Diabetes Care (2003) 26(9):2632-2636.

Gross, J.L., et al., "Diabetic Nephropathy, Diagnosis, Prevention and Treatment," Diabetes Care (2005) Abstract of: 28(1):164-176.

Igarashi, Atsuyuki, et al., "Regulation of Connective Tissue Growth Factor Gene Expression in Human Fibroblasts and During Wound Repair," Mol. Biol. Cell (1993) 4:637-645.

Rivera, F. et al., "Frequency of Renal Pathology in Spain 1994-1999," Nephrol. Dial. Transplant (2002) Abstract of: 17(9):1594-1602.

Tam, Frederick W.K., et al., "Urinary Monocyte Chemoattractant Protein-1 (MCP-1) and Connective Tissue Growth Factor (CCN2) as Prognostic Markers for Progression of Diabetic Nephropathy," Cytokine (2009) 47:37-42.

Wongtim, Somkiat, et al., "Interferon Gamma for Diagnosing Tuberculous Pleural Effusions," Thorax (1999) 54:921-924.

American Diabetes Association, "Data From the 2011 National Diabetes Fact Sheet," Diabetes Statistics (2011) 1-4.

CDC, "Tuberculin Skin Testing," TB Elimination (2010) 1-3.

Diagnostic Automation, Inc., "Enzyme Immunoassay for the Quantitative Determination of Human Growth Hormone (HGH) Concentration in Human Serum," (2009) 1-5.

\* cited by examiner

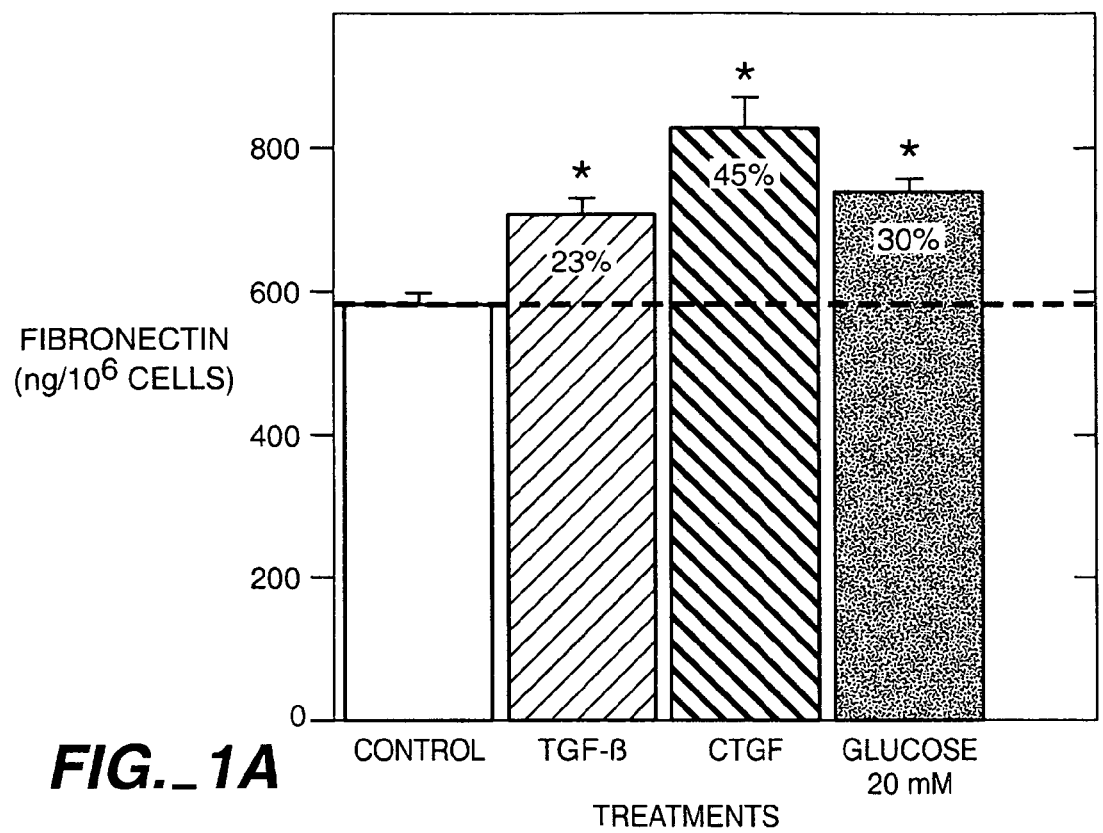
FIG._1A
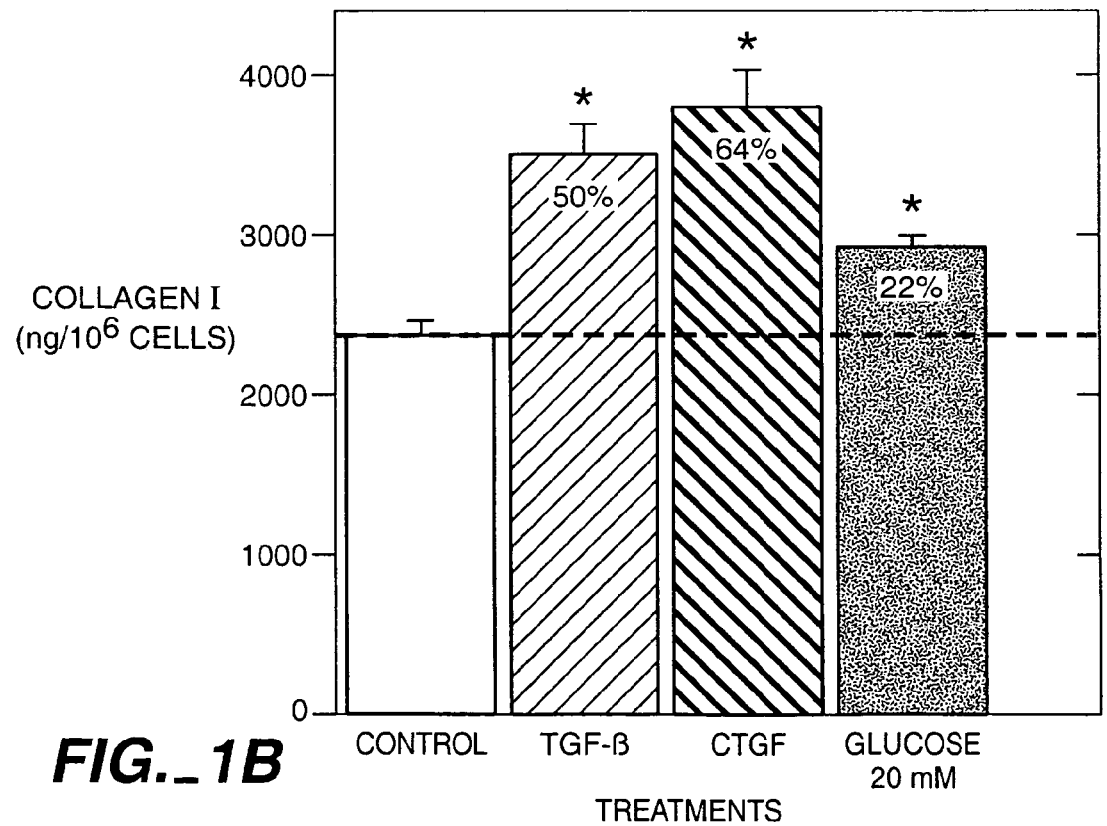
FIG._1B

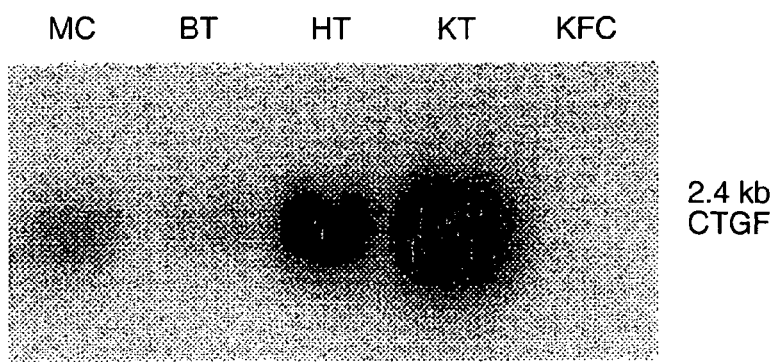
FIG._2
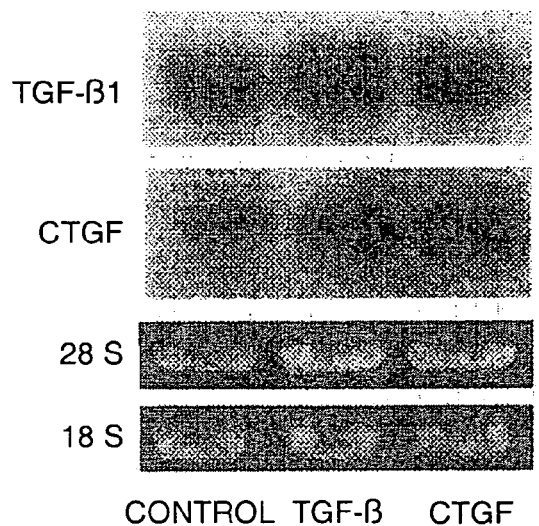
FIG._3A
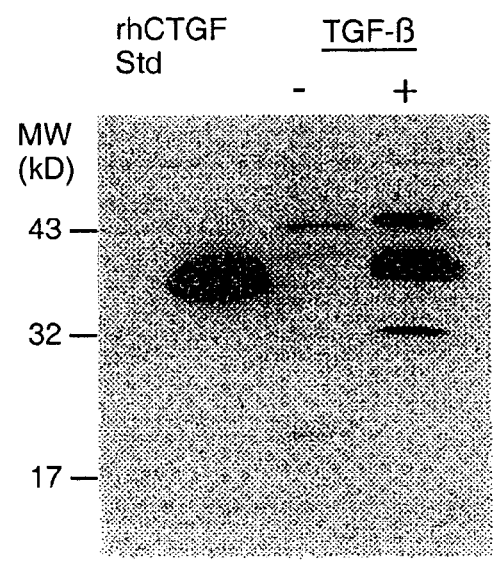
FIG._4A
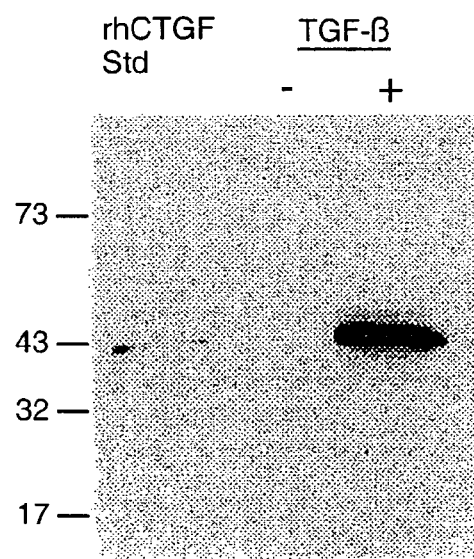
FIG._4B

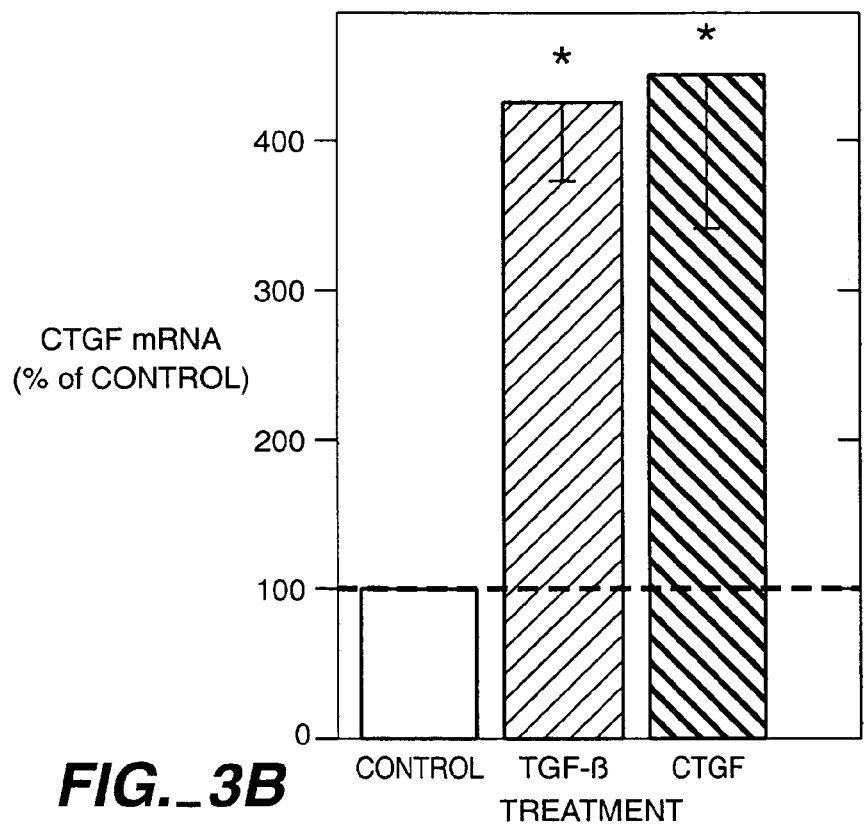
FIG._3B
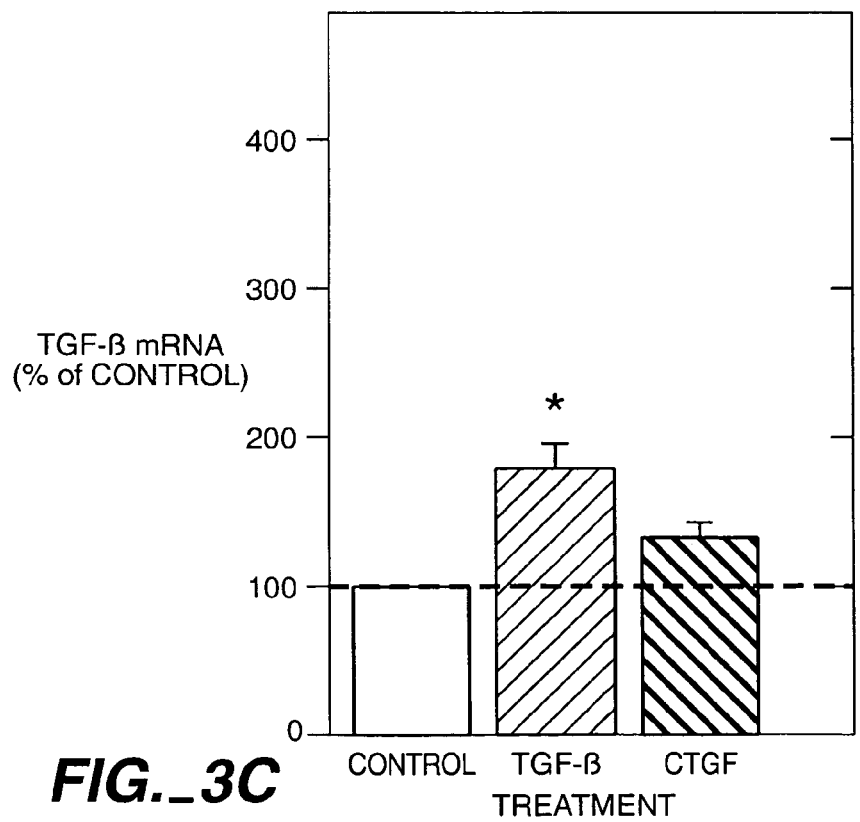
FIG._3C

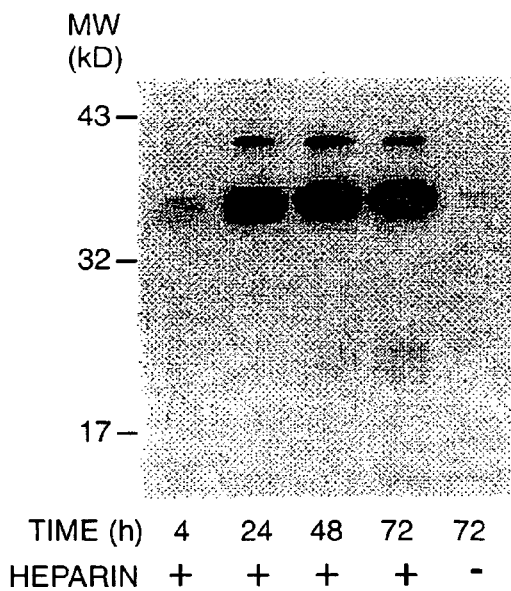
FIG._5A
TIME (h)  4  24  48  72  72
HEPARIN  +  +  +  +  −
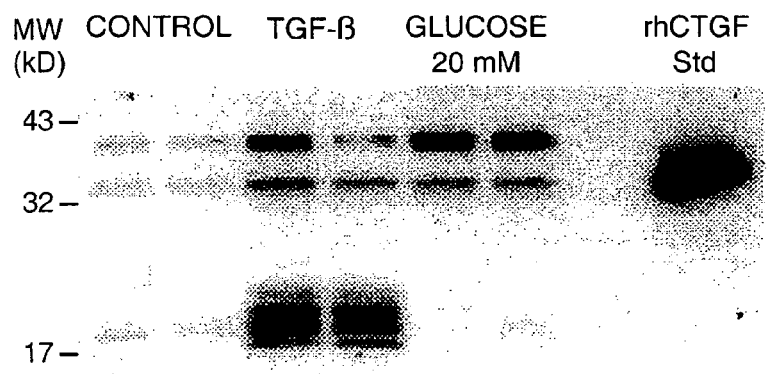
FIG._6A
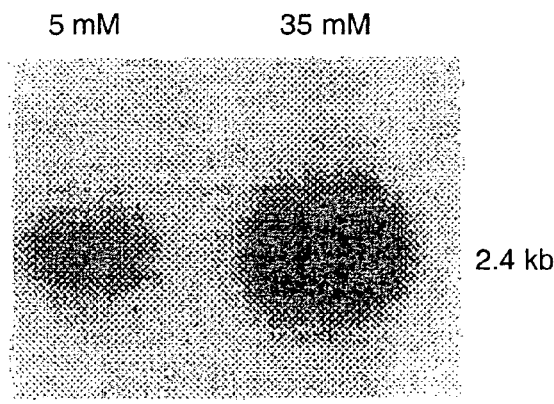
FIG._7A
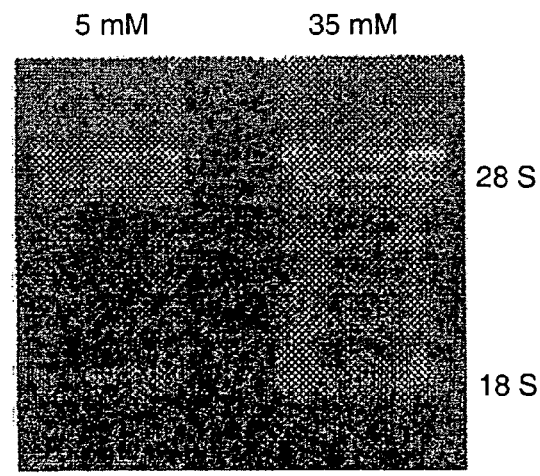
FIG._7B

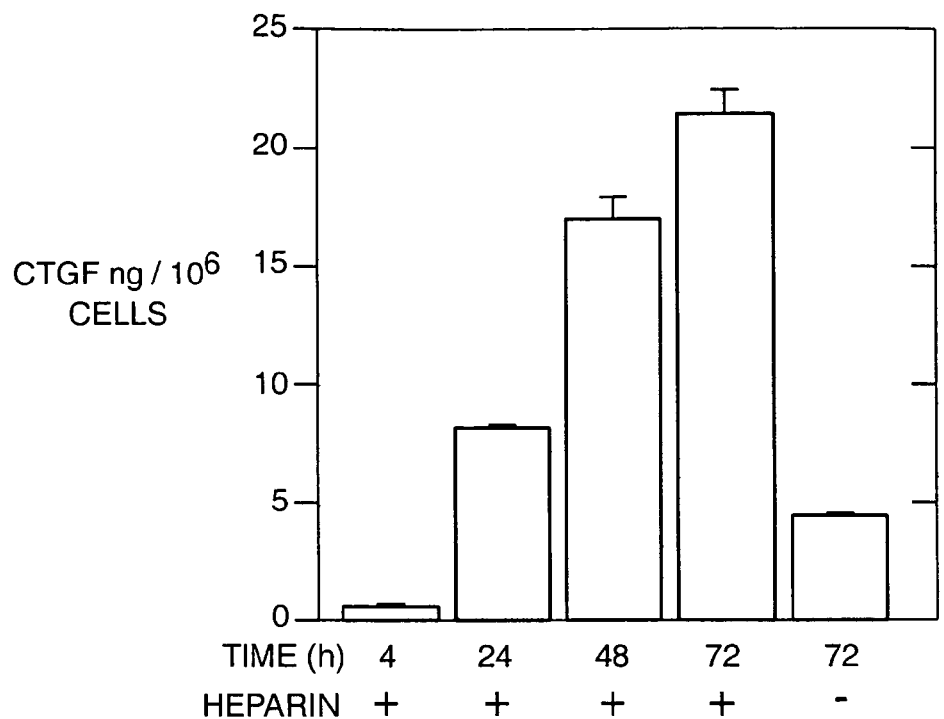
FIG._5B
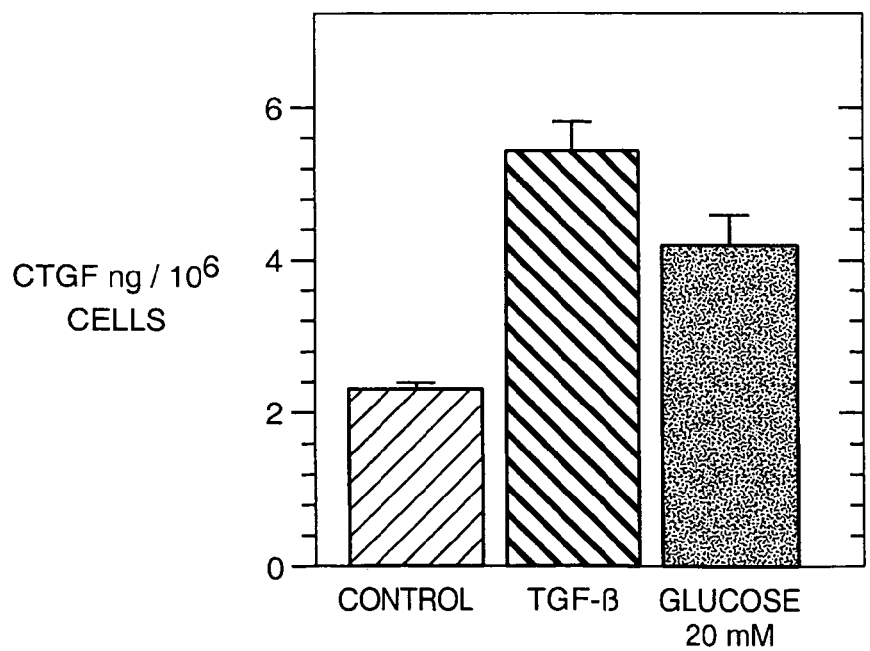
FIG._6B

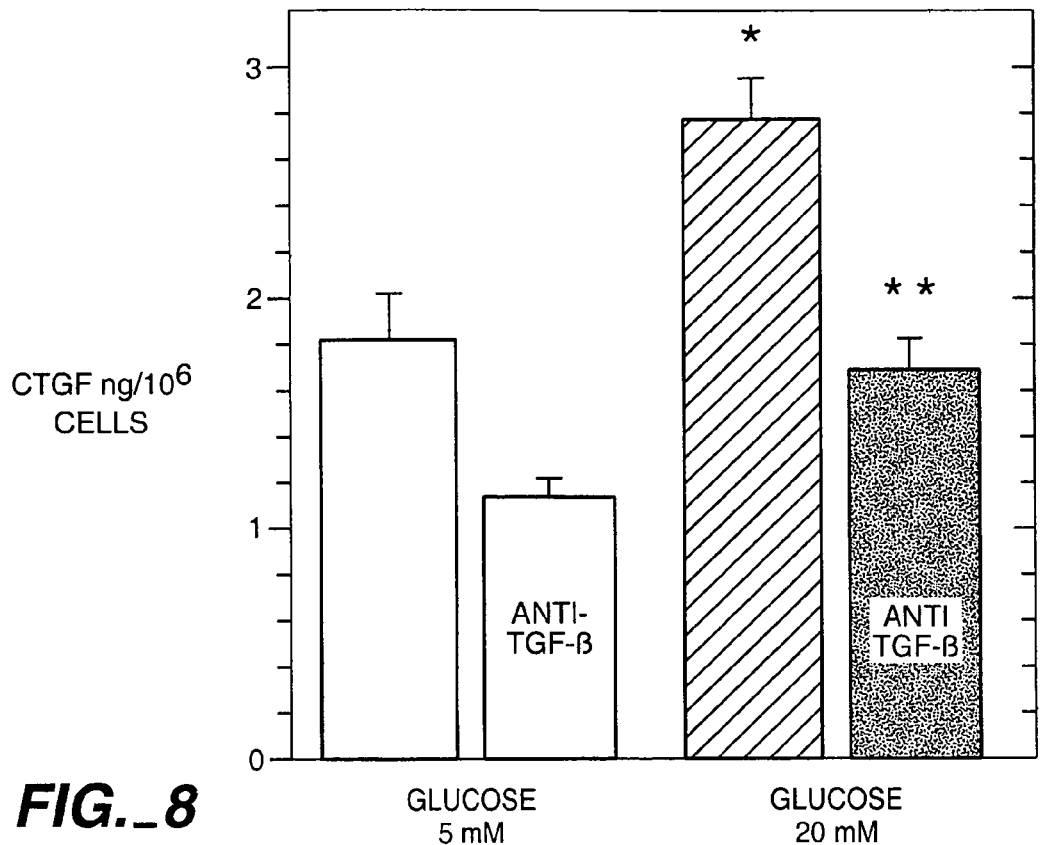
FIG._8
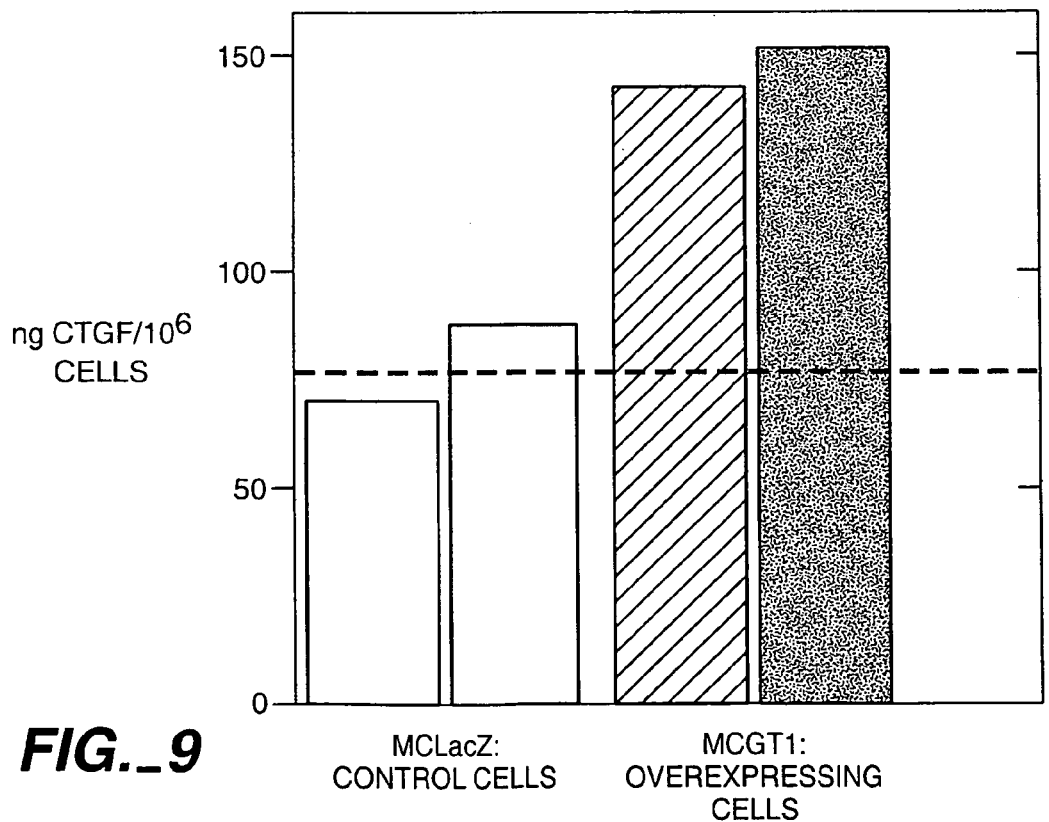
FIG._9

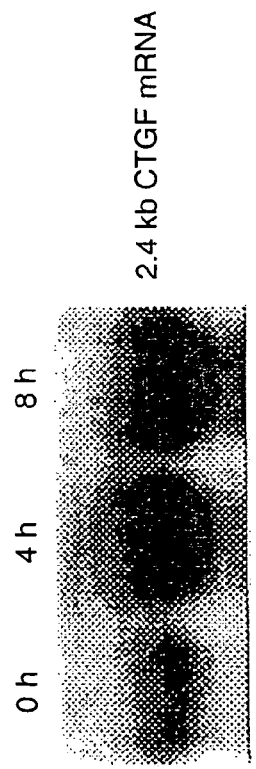
FIG._10A
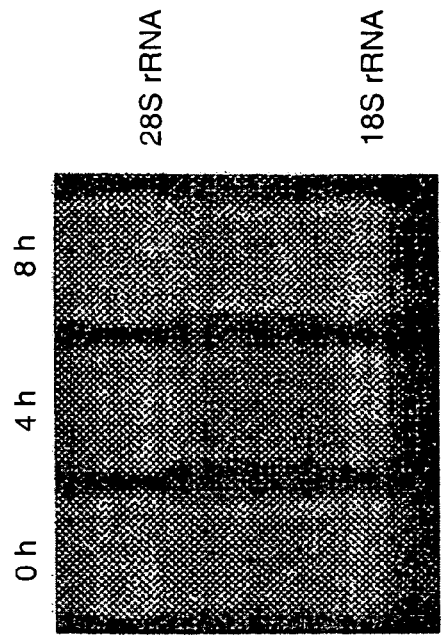
FIG._10B
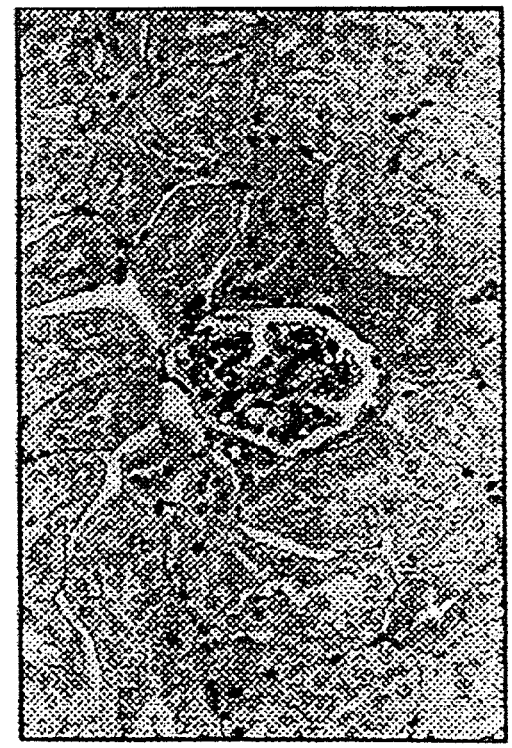
FIG._13A
FIG._13B

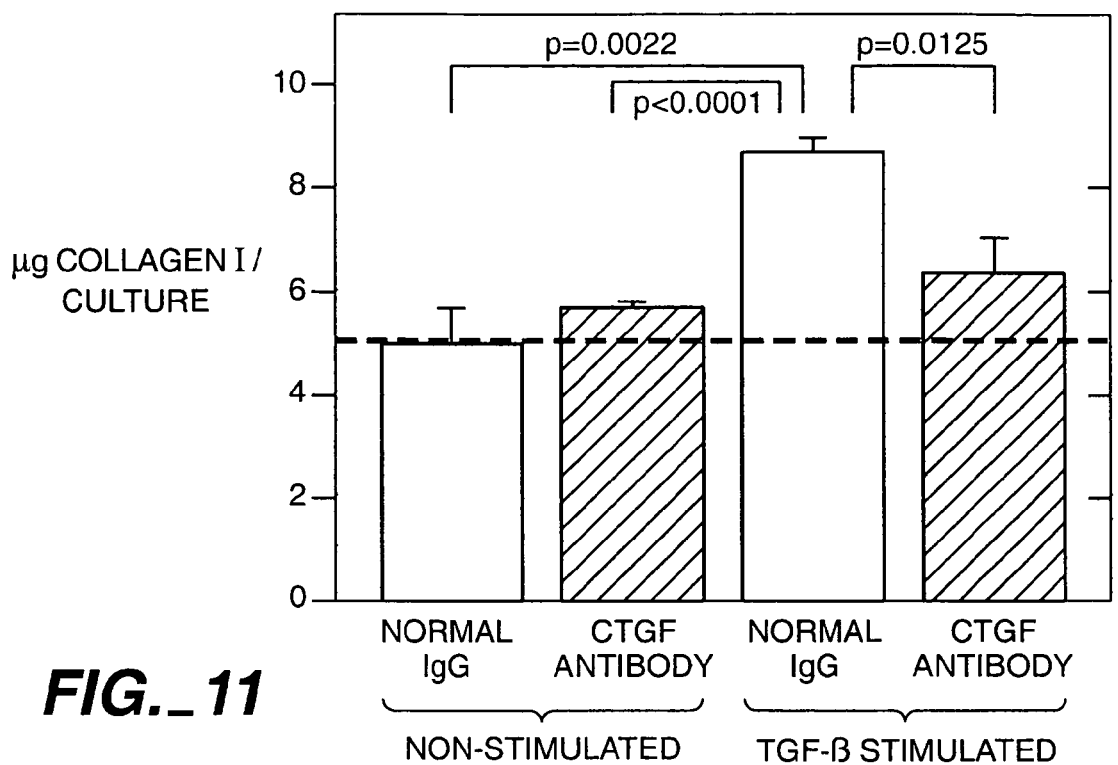
FIG._11
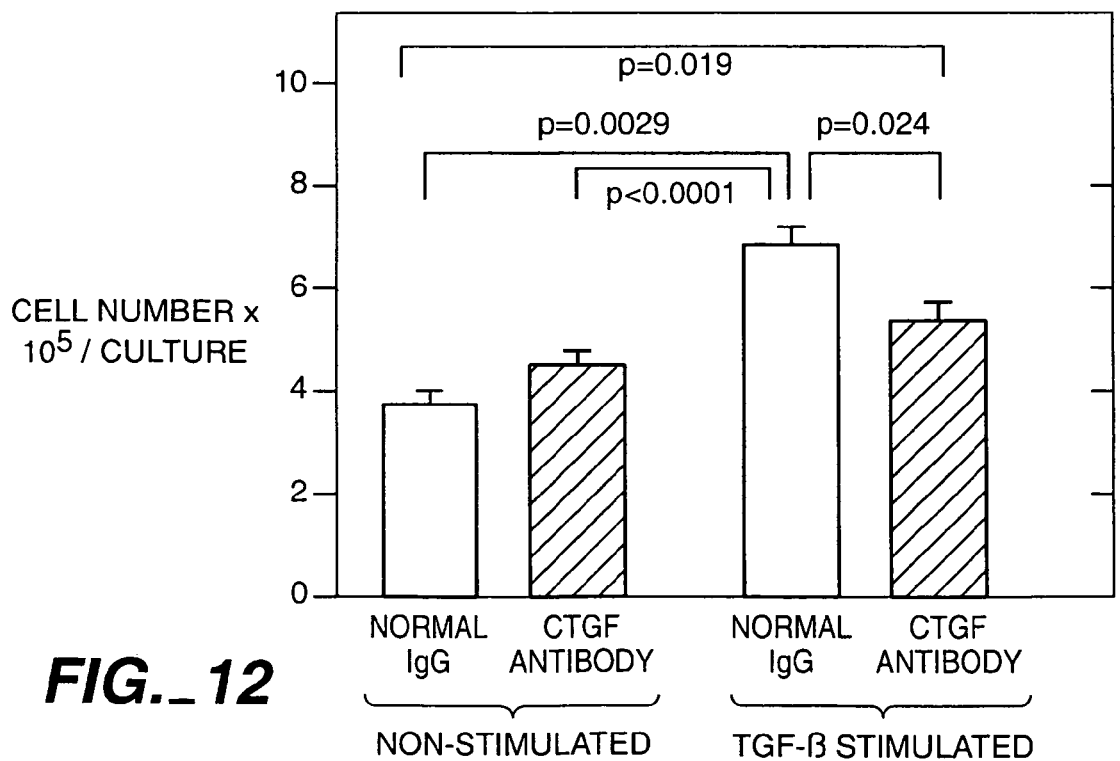
FIG._12

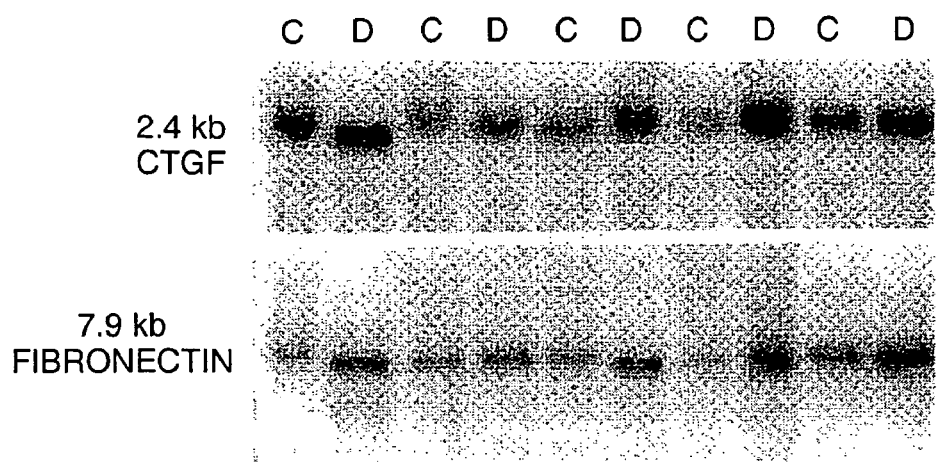
FIG._14A
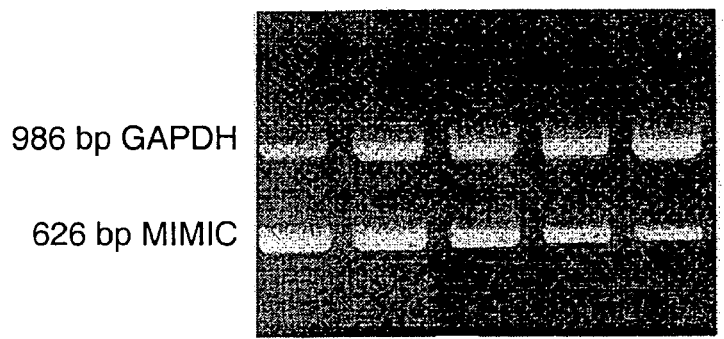
FIG._15A
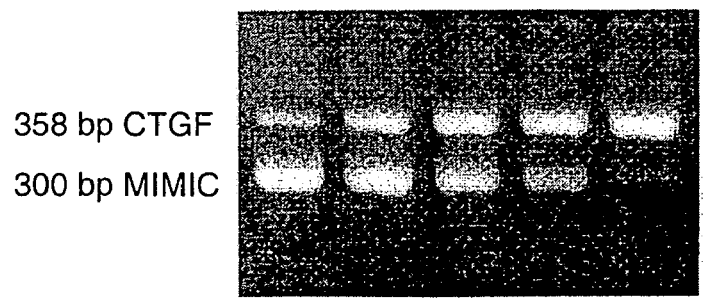
FIG._15B

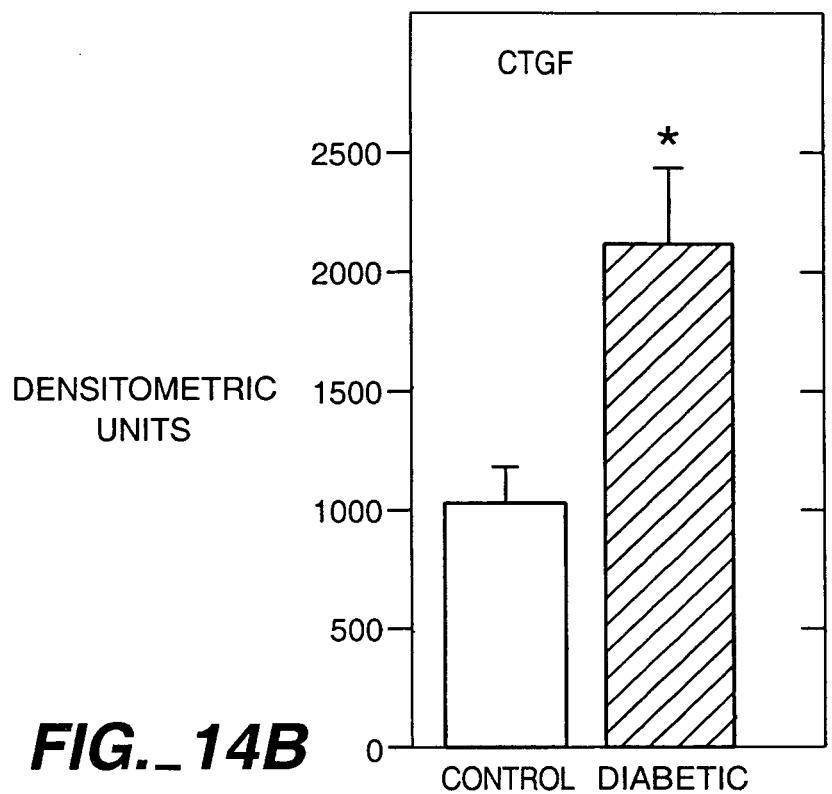
FIG._14B
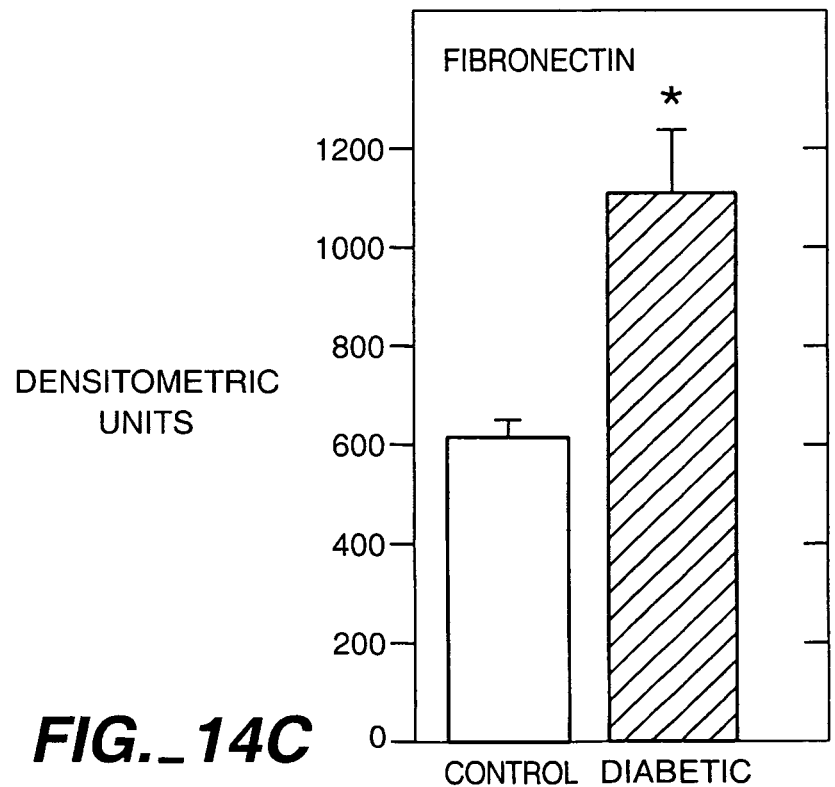
FIG._14C

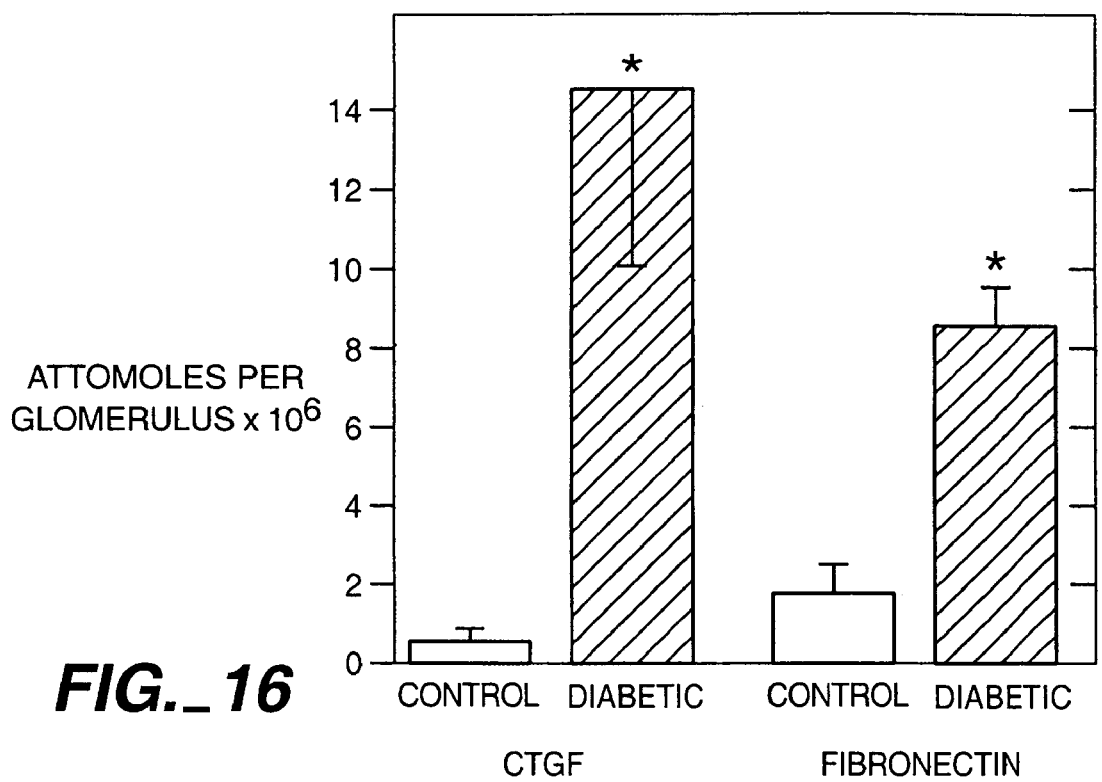
FIG._16

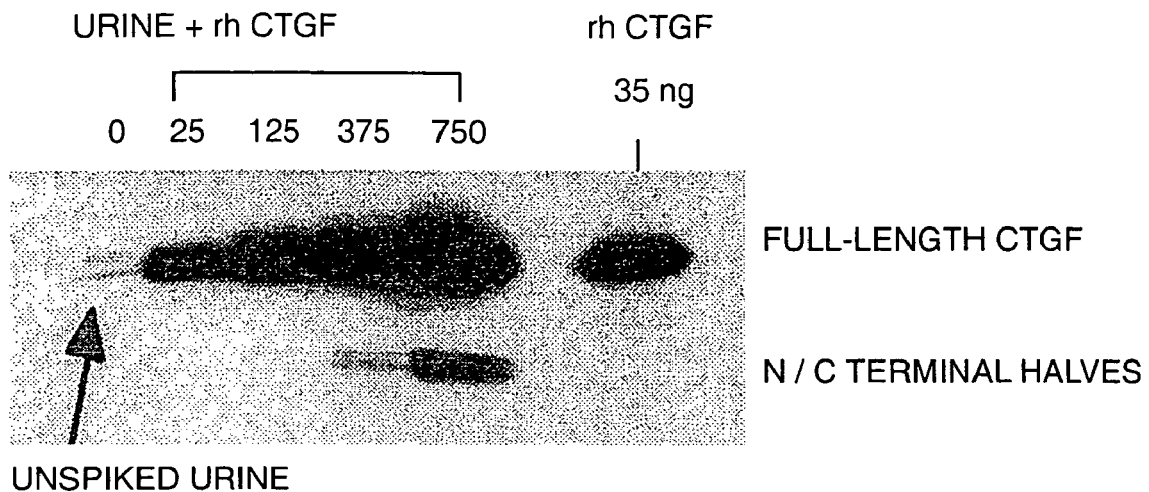
FIG._17
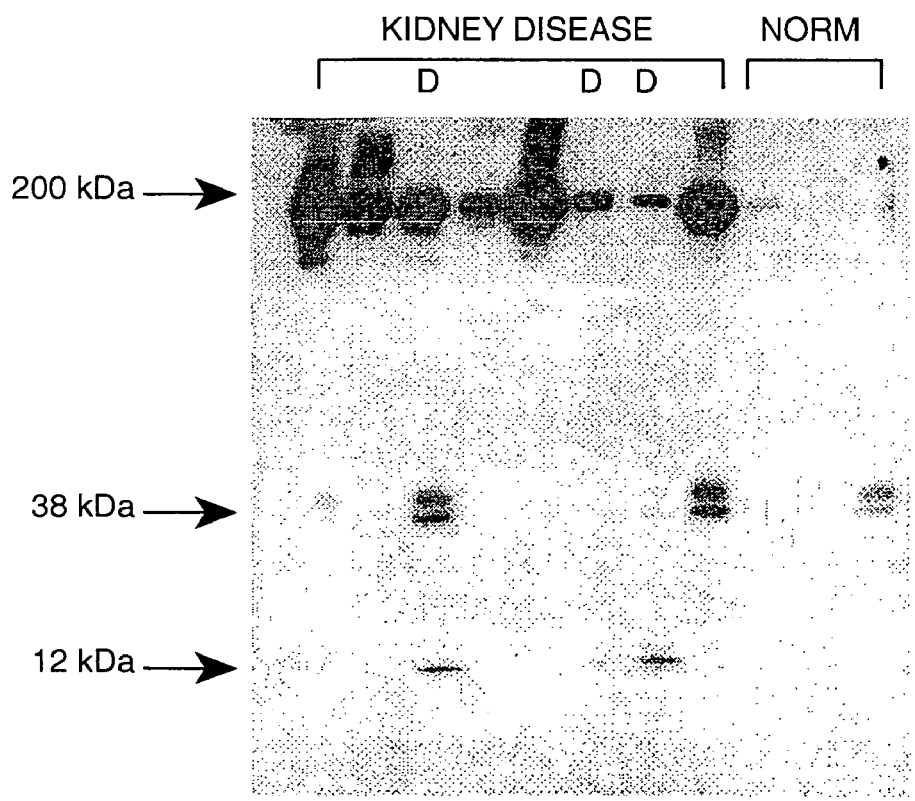
FIG._18

METHODS FOR DIAGNOSING RENAL DISORDERS

This application is a continuation of U.S. patent application Ser. No. 10/687,479 filed on 16 Oct. 2003, which is a continuation of U.S. patent application Ser. No. 09/392,024, filed on Sep. 8, 1999 (now abandoned), and claims the benefit of U.S. Provisional Application Ser. No. 60/112,855, filed on Dec. 16, 1998 and U.S. Provisional Application Ser. No. 60/099,471, filed on Sep. 8, 1998; all of which are incorporated by reference herein in their entirety.

FIELD OF THE INVENTION

The present invention relates to the role of Connective Tissue Growth Factor (CTGF) in the production of extracellular matrix. More specifically, the invention relates to methods of detecting, preventing, and treating kidney fibrosis and other conditions associated with overproduction of the extracellular matrix by targeting CTGF.

BACKGROUND OF THE INVENTION

Kidney Diseases And Disorders. The kidney functions to separate waste products from the blood, regulate acid concentration, and maintain water balance. Kidneys control the levels of various compounds in the blood, such as hydrogen, sodium, potassium, and silicon, and eliminate waste in the form of urine. Any degradation in kidney function can interfere with the body's ability to adequately remove metabolic products from the blood, and can disrupt the body's electrolyte balance. In its most severe forms, degradation or impairment of kidney function can be fatal.

A number of conditions can lead to chronic renal failure, a decline in kidney function over time. For example, such conditions as hypertension, diabetes, congestive heart failure, lupus, and sickle cell anemia have been associated with renal failure. Acute disease processes and injuries can trigger a more immediate decline in kidney function.

It is thus well understood that individuals with diabetes, hypertension, inflammatory and autoimmune diseases, and other disorders are at risk for altered and progressive loss of kidney function characterized by, for example, reduced glomerular filtration, albuminuria, proteinuria, and progressive renal insufficiency. More than half of the total number of kidney disorders initiate kidney fibrosis. Fibrosis involves altered formation or production of fibrous tissue, and can result in the overproduction and increased deposition of extracellular matrix components.

The extracellular matrix (ECM) is a complex network of various glycoproteins, polysaccharides, and other macromolecules secreted from a cell into extracellular space. The ECM provides a supportive framework, directly influencing various cellular characteristics, including shape, motility, strength, flexibility, and adhesion. In fibrosis, overproduction and increased deposition of ECM materials can result in thickening and malformation of various membranous and cellular components, reducing local flexibility and surface area of the affected site, and impairing a number of bodily processes.

Kidney fibrosis is a common pathway in the progression of various forms of renal injury. Kidney fibrosis typically spreads by enlisting previously undamaged regions of the kidney. As normal filtration processes decline, function of surviving tissue and of various regions of the kidney is systematically destroyed. Kidney fibrosis can be manifested as a diffuse thickening of kidney membranous components, the accumulation and expansion leading to a loss of filtration surface area and a corresponding disruption in the body's electrolyte composition and acid-base balance.

Fibrosis of the kidney is observed in a number of conditions, including, for example, diabetic, autoimmune, and transplant nephropathy; hypertension; and certain forms of glomerular injury or disease. Diabetes mellitus (diabetes) is a complex disease that affects several hundred million people worldwide. Diabetes is characterized by hyperglycemia or elevated levels of glucose in the blood. Glucose cannot enter the body's cells to be utilized and therefore remains in the blood in high concentrations. When the blood glucose level exceeds the reabsorptive capacity of the renal tubules, glucose is excreted in the urine. Diabetes produces a number of debilitating and life-threatening complications.

Progressive nephropathy is one of the most frequent and serious complications of diabetes. See, e.g., Hans-Henrik et al., 1988, Diabetic Nephropathy: The Second World Conference on Diabetes Research, New Frontiers. The Juvenile Diabetes Foundation International, pp. 28-33. A hallmark of diabetic nephropathy, and of renal sclerosis due to other forms of renal injury, is early expansion of the glomerular mesangium, largely due to increased accumulation of ECM proteins such as collagen types I and IV, fibronectin, and laminin. See, e.g., Mauer et al., 1984, *J Clin Invest* 74:1143-1155; Bruneval et al., 1985, *Human Pathol* 16:477-484. This pathological deposition results in impaired filtration, leading to renal failure, a condition requiring transplantation or life-long dialysis. Current therapies slow but do not arrest or reverse the progressive loss of kidney function. Predominant causal factors identified to date also include hyperglycemia, glomerular hypertension, and abnormal cytokine environments. Tuttle, et al., 1991, *N Engl J Med* 324:1626-1632; The Diabetes Control Complications Trial Research Group, 1993, *N Engl J Med* 329:977-986; Hostetter et al., 1981, *Kidney Int* 19:410-415; Anderson et al., 1985, *J Clin. Invest* 76; 612-619; Border et al., 1993, *Am J Kidney Dis* 22:105-113.

Hyperglycemia may be damaging, in great part as increased concentrations of glucose stimulate ECM accumulation by mesangial cells. See, e.g., Ayo et al., 1990, *Am. J. Pathol.* 136:1339-1348; Heneda et al., 1991, *Diabetologia* 34:190-200; Nahman et al., 1992, *Kidney Int* 41:396-402; Cortes et al., 1997, *Kidney Int.* 51:57-68. As shown by Davies et al., 1992, *Kidney Intl.* 41:671-678, mesangial cells are largely responsible for mesangial matrix synthesis in situ. It has further been determined that the effect of glucose on mesangial cell matrix production is linked to increased glucose transport and utilization. Helig et al., 1995, *J. Clin. Invest.* 96:1802-1814. Moreover, Ziyadeh et al., 1994, *J. Clin Invest.* 93:536-542, have shown the involvement of secreted soluble mediators on mesangial cell matrix production.

Renal hypertension, which can appear as a secondary manifestation of kidney disease in diabetic patients, can also result from other diseases or disorders, including long-standing hypertension. Secondary hypertension can be caused by virtually any impairment in renal function. A greater understanding of the pathogenic mechanisms for hypertension-induced ECM deposition is developing. For example, in diabetes, an early impairment of normal blood pressure dampening occurs at the glomerular afferent arteriole, resulting in the exposure of glomerular capillaries to large moment-to-moment variations in systemic blood pressure. Hayashi et al., 1992, *J Am Soc Nephrol* 2:1578-1586; Bidani et al., 1993, *Am J Physiol* 265:F391-F398. Due to the elasticity of the glomerulus, increased capillary pressure produces expansion of glomerular structure, resulting in augmentation of the mechanical strain imposed on the mesangial cells. Riser et al., 1992, *J Clin Invest* 90:1932-1943; Kriz et al., *Kidney Int Suppl* 30:S2-S9. In addition, when cultured mesangial cells are subjected to cyclic strain, the mesangial cells respond by increasing the synthesis and accumulation of collagen types I and IV, fibronectin, and laminin. Riser et al., 1992, supra. While increased glomerular pressure is common in diabetes, it is not limited to this disease, and is present in other forms of progressive renal disorders, including, for example, certain forms of glomerular nephritis and hypertrophy. See, e.g., Cortes et al., 1997, *Kidney Int* 51:57-68.

Kidney fibrosis and associated renal impairment are thus present in the progression of various diseases and disorders, including diabetes and hypertension, and methods of treating kidney fibrosis are thus greatly desired.

Transforming Growth Factor β (TGF-β). The few studies conducted to date regarding the physiological implications of renal disorders and diseases, and, in particular, those due to diabetes, have focused on the role of transforming growth factor-β (TGF-β) in developing methods for targeting overproduction (increased synthesis and accumulation) of extracellular matrix components. The role of cytokine imbalance in initiating and/or perpetuating glomerular matrix expansion has been explored in experimental nephropathy studies involving TGF-β. See, e.g., Sharma et al., *Seminars In Nephrology* 1: 116-129. Glomerular TGF-β activity is increased in both human and experimental diabetic glomerulosclerosis. See, e.g., Yamamoto et al., 1993, *Proc Natl Acad Sci* 90:1814-1818; Sharma et al., 1994, *Am J Physiol* 267:F1094-F1101; Shankland et al., 1994, *Kidney Int* 46:430-442. The exposure of cultured mesangial cells or glomeruli to TGF-β results in increased ECM production. See, e.g., Bollineni et al., 1993, *Diabetes* 42:1673-1677. In vivo induction of glomerular matrix accumulation following transfection and overexpression of the TGF-β gene in rat kidney has been demonstrated by, for example, Isaka et al., *J Clin Invest* 92:2597-2601.

In addition, neutralization studies have shown that anti-TGF-β antibody mitigates the enhanced glomerular ECM gene expression that occurs in experimental glomerulonephritis and diabetes. Border et al., 1990, *Nature* 346:371-374; Sharma et al., 1996, *Diabetes* 45:522-530. The sustained overexpression of glomerular TGF-β in diabetes may be the result of a mesangial cellular response to both increased glucose levels and hypertension. It has been reported that exposure of mesangial cells to increased concentrations of glucose in the medium stimulates the synthesis and release of TGF-β1, as well as the increased binding of TGF-β to specific receptors. Ziyadeh et al., 1994, *J Clin Invest* 93:536-542; Riser et al., 1998, *J Am Soc Nephrol* 9:827-836; Riser et al., 1999, *Kidney Int* 56:428-439. It has also been reported that mechanical force selectively stimulates the production, release, and activation of TGF-β1, as well as the increased expression of TGF-β receptors. Riser et al., 1996, *Am J Path* 148:1915-1923.

In vitro neutralization studies of TGF-β demonstrated a significant reduction of collagen synthesis induced in mesangial cells by increased glucose levels. See, e.g., Sharma et al., 1996, supra; Ziyadeh et al., 1994, supra. Studies have also shown a virtual elimination of collagen accumulation resulting from cyclic stretching in the presence of excess glucose. Riser et al., 1997, supra. TGF-β stimulates the proliferation of mesangial cells in vitro and in vivo, and may induce in these replicating cells overproduction and increased deposition of ECM characteristic of various renal disorders, including proliferative disorders such as glomerular nephritis. See, e.g., Border et al., 1990, *Nature* 346:371-374; Habershroh et al., 1993, *Am J Physiol* 264:F199-205. As a result of these findings, intense efforts have been directed toward reducing TGF-β availability and binding as a means of mitigating matrix accumulation. However, the ubiquitous nature and pluripotent functions of TGF-β, including tumor suppression and the multiple levels of regulation, raise questions concerning both the feasibility and the safety of its long-term inhibition. See, e.g., Brattain et al., 1996, *Curr Opin Oncol* 8:49-53; Franklin, 1997, *Int J Biochem Cell Biol* 29:79-89.

Therefore, a method for treating or preventing ECM overproduction or increased deposition, without interfering with the ubiquitous function of TGF-β, is needed.

Connective Tissue Growth Factor (CTGF). CTGF is a peptide that may act downstream of TGF-β to regulate matrix accumulation. This novel growth factor has been reported and described previously. See, e.g., U.S. Pat. No. 5,408,040; Bradham et al., 1991, *J Cell Biol* 114:1285-1294. CTGF is characterized as a polypeptide which exists as a monomer with a molecular weight of approximately 36 to 38 kD. CTGF has been shown to be one of seven cysteine-rich secreted proteins belonging to the CCN family, which includes CTGF, cyr-61, and nov. Oemar et al., 1997, *Arterioscler Thromb Vasc Biol* 17(8):1483-1489. CTGF is an immediate early response gene that codes for a protein consisting of four modules and one signal peptide. Oemar et al., 1997, supra. The four modules are: 1) an insulin-like growth factor (IGF) binding domain, 2) a von Willebrand factor type C repeat most likely involved in oligomerization, 3) a thrombospondin type 1 repeat believed to be involved in binding to the ECM, and 4) a C-terminal module which may be involved in receptor binding. Recent reports suggest that certain fragments of the whole CTGF protein possess CTGF activity. See, e.g., Brigstock, et al., 1997, *J Biol Chem* 272(32):20275-20282. Human, mouse, and rat CTGF are highly conserved with greater than 90% amino acid homology and a molecular weight of about 38 kD. It was recently shown that the promoter of CTGF contains a novel TGF-β responsive element. Grotendorst et al., 1996, *Cell Growth Differ* 7:469-480.

It appears that CTGF may be an important prosclerotic molecule in both skin fibrosis and cardiac atherosclerosis. For example, CTGF mRNA is expressed by fibroblasts in the lesions of patients with systemic sclerosis, keloids, and localized scleroderma, while there is no corresponding expression in adjacent normal skin. See, e.g., Igarashi et al., 1995, *J Invest Dermatol* 105:280-284; Igarashi et al., 1996, *J Invest Dermatol* 106:729-733. Cultured normal human skin fibroblasts respond to TGF-β but not to platelet-derived growth factor (PDGF), epidermal growth factor (EGF), or basic fibroblast growth factor (bFGF), by increasing levels of CTGF mRNA and CTGF protein. Igarashi et al., 1993, *Mol Biol Cell* 4:637-645. Fibroblasts from lesions of scleroderma show increased mitogenesis to TGF-β and produce greater amounts of CTGF than do normal fibroblasts. Kikuche et al., 1995, *J Invest Dermatol* 105:128-132. Recombinant human CTGF injected under the skin of NIH Swiss mice induces the same rapid and dramatic increase in connective tissue cells and ECM as occurs with TGF-β treatment, whereas PDGF and EGF have little or no effect on granulation. Frazier et al., 1996, *J Invest Dermatol* 107:404-411. Cultured vascular smooth muscle cells are also stimulated by TGF-β to produce CTGF. In heart disease patients, CTGF mRNA is expressed at levels 50- to 100-fold higher in atherosclerotic plaques than in normal arteries. Oemar et al., 1997, *Circulation* 95(4):831-839.

In spite of mounting evidence implicating CTGF as a causal factor in skin fibrosis and cardiac atherosclerosis, very little is known of its expression in, for example, renal sclerosis or diabetes. It has been shown, using an in vitro model of calcium oxalate nephrolithasis, that monkey kidney epithelial cells respond to calcium oxalate by upregulating the CTGF gene along with other genes involved in matrix turnover. Hammes et al., 1995, *Kidney Int* 48:501-509. A similar response occurs in cultured renal epithelial cells following mechanical wounding. See, e.g., Pawar et al., 1995, *J Cell Physiol* 165:556-565. Most recently, CTGF mRNA was found in biopsies from normal human kidneys. A qualitative assessment indicated that, in a limited number of cases, CTGF expression was increased in the tissues of patients with severe mesangial proliferative lesions of crescentic glomerulonephritis, focal and segmented glomerulosclerosis, and, in three cases, diabetic glomerulosclerosis. Ito et al., 1998, *Kidney Int* 53:853-861. The research, relying only on data obtained from biopsies, did not include quantitative results or any measurement of CTGF protein levels. Further, no connection between CTGF mRNA levels and the production and deposition of ECM, and no quantitative method for detecting renal disorders or diseases, including diabetes, involving a determination of CTGF levels in samples, and did not identify CTGF-expressing cells.

The role of CTGF in kidney diseases is thus unclear, and there has been no research to date has shown that CTGF is causally related to ECM overproduction and increased deposition and to fibrosis in the kidney.

Diagnostics and Early-Stage Detection. Kidney failure is a serious condition requiring extreme treatment such as hemodialysis or transplantation. Early-stage detection and/or prevention of any deviation from normal kidney pathology and function could minimize the risk of a subject's developing a more serious condition. Hypertension, for example, might be undetectable by a patient in early stages, but can be deadly if not identified, monitored, and treated. In addition, in some diseases, such as, for example, diabetes, less invasive and disruptive and more affordable means of treatment, such as dietary modification, are effective only at early stages. Therefore, there is a critical need for effective and reliable methods of diagnosis that permit early stage detection, and corresponding prevention, of renal complications.

For example, kidney failure resulting from progressive glomerulosclerosis is the leading cause of morbidity and mortality among patients with type I, or juvenile, diabetes mellitus. See, e.g., Dorman et al., 1984, *Diabetes* 33:271-276; Anderson et al., 1983, *Diabetologia* 25:496-501. Current therapy with angiotensin-converting enzyme (ACE) inhibitors, the drug class of choice, effectively slows the progression of disease. See, e.g., Lewis et al., 1993, *N Eng J Med* 329:1456-1462. Nevertheless, this treatment is not justified in all newly diagnosed diabetic patients because only approximately 30-35% of these develop progressive kidney disease, and the long-term side effects of these drugs are uncertain. See, e.g., Parving and Hommel, 1989, *Brit Med J* 299:230-233. In addition, ACE inhibitors are also presently used to treat patients with hypertensive renal failure, including that resulting from non-diabetic nephropathies. However, the mechanism of renal protection, and, as noted above, the long-term side effects of this treatment are not fully understood. Furthermore, ACE inhibitors have been shown to negatively interact with nonsteroidal anti-inflammatory drugs. See, e.g., Whelton, 1999, *Am J Med* 106(SB):13S-24S.

In a current method of diagnosis, diabetic patients are monitored for microalbuminuria. Persistent microalbuminuria is a marker of widespread vascular damage and indicates the presence of early nephropathy in type 1 and type 2 diabetes. See, e.g., Stehouwer et al., 1992, *Lancet* 340:319-323; Bojestig et al., 1996, *Diabetes Care* 19:313-317; Mogensen et al., 1995, *Lancet* 346:1080-1084. However, the actual level of microalbuminuria may not necessarily predict the development of overt nephropathy, particularly among patients with a long duration of diabetes. Bojestig et al., supra. In addition, since by the time microalbuminuria is detected, structural renal lesions are already present, the effectiveness of treatment to slow progression may be substantially reduced. Bangstad et al., 1993, *Diabetologia* 36:523-529; Ruggenenti et al., 1998, *J Am Soc Nephrol* 9:2157-2169; Fioretto et al., 1995, *Kidney Int* 48:1929-1935. There is a great need to be able to predict which patients with type 1 diabetes will develop nephropathy, and to, in general, develop a method that will detect renal alterations that may precede the onset of significant disease.

In summary, there is a need in the art for effective methods for diagnosing, treating, and preventing fibrosis associated with impairment and degradation of kidney function in a variety or diseases and disorders, most particularly, in diabetes and hypertension. No current research has focused on the modulation of CTGF expression or activity as a means of preventing or treating kidney fibrosis.

SUMMARY OF THE INVENTION

The present invention satisfies the need in the art by providing methods for detecting, treating, and preventing renal disorders and diseases associated with fibrosis. In particular, the present invention provides methods for detecting, preventing, and treating pathologies and complications associated with renal disorders and conditions which are characterized by an overproduction or increased deposition of extracellular matrix.

Methods Of Treatment and Prevention. The present invention provides various approaches directed to modulation of the overproduction of the extracellular matrix resulting in fibrosis. Specifically, the present invention provides methods of regulating increased accumulation of the extracellular matrix associated with kidney fibrosis as found in various renal diseases and disorders. These renal diseases and disorders include, but are not limited to, all kinds of nephropathy, including glomerulonephritis, glomerulosclerosis, and conditions resulting from glomerular injury; diabetic nephropathy and other complications; nephritis; interstitial disease; acute and chronic transplant rejection; renal hypertension, including that associated with diabetes; and other underlying causes of fibrosis. More specifically, the present invention provides methods for preventing and treating complications associated with the above-named renal disease and disorders by regulating, modulating, and/or inhibiting the expression and activity of CTGF. In particular embodiments, the present methods are directed to the diagnosis, prevention, and treatment of renal diseases and disorders associated with diabetes or with hypertension.

The methods of the present invention provide for the administration of a therapeutically effective amount of an agent that regulates, modulates, and/or inhibits the ECM-producing activity of CTGF. In particular, the methods of this invention are useful for the treatment and prevention of renal disorders in mammals, most preferably, in humans.

In one aspect, the invention provides a method of treating complications associated with diabetes characterized by the overproduction or overaccumulation of the extracellular matrix by administering a therapeutically effective amount of an antibody reactive with a CTGF polypeptide or fragments thereof, or an antigen-binding fragment of an antibody reactive with the CTGF polypeptide or fragments thereof.

In another aspect, the present invention provides a method for treating and preventing complications associated with renal disorders, particularly, diabetes and hypertension, wherein antisense oligonucleotides which specifically bind to CTGF mRNA are used to interrupt expression of the protein product. The antisense oligonucleotides have a sequence capable of binding specifically with any polynucleotide sequences encoding CTGF or fragments thereof.

In yet a further embodiment of the present invention, a method is provided in which small molecules are used to inhibit the activity of CTGF or its active fragments by blocking the binding of CTGF to its receptor, inhibiting CTGF activity and thus thereby reducing the overproduction of the extracellular matrix associated with the onset and/or progression of renal disorders, including diabetes and hypertension.

The present invention further provides a method of treating and preventing renal disorders by administering a compound that blocks the binding interactions of or the enzymes involved in the signal transduction pathway of CTGF.

The present invention also provides a method for treating and preventing diabetes by administering insulin and an agent that modulates and/or inhibits the activity of CTGF. More specifically, the present invention discloses a method for treating and preventing diabetes by administering insulin and an agent that modulates, regulates, and/or inhibits the activity of CTGF according to the methods of the present invention.

Methods for evaluating the effectiveness of anti-fibrotic therapy, including the use of ACE inhibitors, by measuring the levels of CTGF in a sample from a subject undergoing a course of treatment for diseases and disorders associated with fibrosis, are also provided.

Diagnostic Methods. The present invention is also directed to methods for predicting which patients with diseases and disorders associated with renal disorders will subsequently develop progressive kidney disease. In one embodiment, the invention provides a method for detecting and/or staging (classifying the level, site, and spread of disease) kidney involvement in a particular disease or disorder. In one embodiment, a method of predicting whether a patient with diabetes will go on to develop progressive kidney disease is provided, along with a method of detecting the current level of kidney involvement, for example, in a subject with diabetes as opposed to a subject without diabetes.

The present invention is also directed to methods of detecting the presence of pathology of a tissue characterized by an excessive accumulation of extracellular matrix components. In one embodiment, the method involves determining the levels of CTGF, for example, through tissue biopsy or through non-intrusive methods, such as, for example, collection of a urine sample. In a particular embodiment, the method comprises determining the levels of CTGF in a sample comprising, for example, urine or other bodily fluids from a subject with a diabetic nephropathy, such as, for example, diabetic glomerulosclerosis. The method can also comprise determining the levels of CTGF in persons with progressive sclerosis, both with and without diabetes, by determining the levels of CTGF in urine or in other bodily fluids.

More specifically, the present invention comprises a means of diagnosing the presence of or a predisposition to kidney diseases and disorders, including a means for detecting and monitoring the pathogenesis of these diseases and disorders, or for detecting and monitoring the presence of markers for the pathogenesis of these diseases and disorders. More specifically, the present invention provides for diagnosing renal disorders by measuring the levels of CTGF in a patient sample, preferably, in a urine sample from a patient.

In one embodiment of the present invention, a method is provided for the measurement of CTGF levels in a sample from a patient with no known or with a suspected renal disorder. Comparison of CTGF levels in urine samples from a patient known to have a kidney disease or disorder, or from a patient known not to have any kidney disease or disorder, with CTGF levels in urine samples from a patient with no known or with a suspected kidney disorder can be indicative of the presence of a kidney disease or disorder. In particular, the method provides that higher levels of CTGF are present in samples from patients having renal disorders than in samples from patients without any renal disorder. Higher levels of CTGF are thus indicative of the presence of a disease or disorder associated with kidney fibrosis.

In another embodiment, the levels of CTGF can be measured by detecting CTGF mRNA or protein in a sample. In a further embodiment, the sample is a tissue sample and the presence of CTGF is detected by staining of the protein in the tissue or by determination of CTGF mRNA levels.

A preferred method of the present invention utilizes an antibody, preferably, a monocolonal antibody, capable of specifically binding to CTGF or active fragments thereof. The method of utilizing an antibody to measure the levels of CTGF allows for non-invasive diagnosis of the pathological states of kidney diseases. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of CTGF in sample. In a particular embodiment, the antibodies of the present invention are used to detect and to measure the levels of CTGF present in a urine sample.

Diagnostic Kit. The present invention is further directed to diagnostic kits for detecting and measuring the levels of CTGF in a sample in order to detect a renal disorder or a predisposition to a renal disorder in a subject. In one embodiment, the kit contains antibodies specific for CTGF and reagents for detecting and measuring CTGF in a sample. The sample can be a bodily fluid, such as urine, or, for example, a tissue sample. In one embodiment of the present invention, the kit comprises an immobilized antibody which specifically recognizes CTGF and an antibody specific for CTGF and capable of binding to an antigen component different from the immobilized antibody. The CTGF antibody can be enzyme-labeled, radio-labeled, or fluoroscein-labeled. The kit can also comprises reagents necessary for detection of the antibody, and can further comprise other reagents as desired, such as, for example, dissolving agents, cleaning agents, and reaction terminators.

In a preferred embodiment of the invention, the kit is packaged, for example, in a box or a container which includes the necessary elements of the kit, and also includes instructions relating to the use of the kit.

BRIEF DESCRIPTION OF THE DRAWINGS

FIG. 1A and FIG. 1B depict the effects of exogenous CTGF on mesangial cell secretion of the extracellular matrix. FIG. 1A shows the quantities of fibronectin contained in the media at the end of incubation determined by ELISA. FIG. 1B shows the quantities of collagen type I contained in the media at the end of incubation determined by ELISA.

FIG. 2 depicts CTGF gene expression in rat tissues and cultured kidney cells. Total RNA was extracted from whole organs of rat and from cultured rat mesangial cells and kidney fibroblasts for Northern analysis. MC represents mesangial cells; BT represents brain tissue; HT represents heart tissue; KT represents kidney tissue; and KFC represents kidney fibroblast cells.

FIG. 3A, FIG. 3B, and FIG. 3C depict regulation of CTGF and TGF-β mRNA levels by exogenous TGF-β and CTGF.

FIG. 3A shows results from a representative experiment. FIG. 3B shows quantitation of mRNA bands for CTGF. FIG. 3C shows quantitation of mRNA bands for TGF-β.

FIG. 4A and FIG. 4B depict expression of CTGF protein by culture mesangial cells in the presence of exogenous TGF-β. FIG. 4A shows immunoblotting using an antibody raised against full length CTGF. FIG. 4B shows immunoblotting using an antibody raised against a 15 amino acid sequence specific to CTGF.

FIG. 5A and FIG. 5B depict secretion of CTGF protein into the medium of mesangial cell cultures, and the effect of heparin. FIG. 5A shows data relating to media pooled and heparin-sepharose treated for immunoblotting. FIG. 5B shows data relating to media tested for CTGF content individually by ELISA prior to pooling.

FIG. 6A and FIG. 6B depict CTGF protein induction by mesangial cells. FIG. 6A shows data relating to media pooled and heparin-sepharose treated for immunoblotting. FIG. 6A shows data relating to media tested for CTGF content individually by ELISA prior to pooling.

FIG. 7A and FIG. 7B depict the effect of high glucose concentration on mesangial cells expression of CTGF mRNA. FIG. 7 shows samples of pooled RNA from 6 different 100 mm culture dishes in a representative experiment.

FIG. 8 depicts TGF-β blockade of high glucose-induced CTGF production using anti-TGF-β antibody.

FIG. 9 depicts CTGF concentrations in mesangial cells overexpressing different levels of GLUT1. Supernatants from duplicate culture cells transduced with the GLUT1 gene denoted MCGT1 or a transfection control LaZ gene (MCLaZ).

FIG. 10A and FIG. 10B depict the effect of cyclic stretching on mesangial cell expression of CTGF transcripts. At the indicated periods, RNA was extracted and probed for CTGF message. Each lane represents the results of the samples pooled from 24 different culture wells.

FIG. 11 depicts blockade of stimulated collagen type I production by an anti-CTGF antibody.

FIG. 12 depicts blockade of stimulated mesangial cell proliferation by anti-CTGF antibody.

FIG. 13A and FIG. 13B depict glomerular disease associated with diabetes in db/db mice. FIG. 13A shows renal cortical section from control db/m mice at 5 months of age. FIG. 13B shows renal cortical section from diabetic db/db mice at 5 months of age. The sections from FIG. 13A and FIG. 13B were stained with PAS for light microscopy examination, and are examples of glomeruli demonstrating the most severe mesangial expansion observed in the diabetic group.

FIG. 14A, FIG. 14B, and FIG. 14C depict induction of CTGF and fibronectin transcripts in whole kidney of diabetic db/db mice at 5 months of age. FIG. 14A shows total RNA extracted from whole kidneys and probed by northern analysis for CTGF mRNA and fibronectin mRNA, respectively. The letter "C" represents nondiabetic mice, while the letter "D" represents diabetic mice. FIG. 14B and FIG. 14C show quantification by denositometric analysis of the results of the Northern analyses.

FIG. 15A and FIG. 15B depict competitive RT-PCR for GAPDH and CTGF mRNA in a single sample from diabetic mouse glomeruli. Ethidium bromide-stained gel after PCR amplification. The lanes of FIGS. 15A and 15B contain a constant amount of test cDNA and 2-fold decreasing concentrations of a known amount of the specific mimic. FIG. 15A shows competitive reverse transcriptase PCR(RT-PCR) for GAPDH. FIG. 15B shows competitive RT-PCR for CTGF.

FIG. 16 depicts the effects of diabetes on the glomerular expression of CTGF and fibronectin transcript levels in db/db mice, detected by competitive RT-PCR.

FIG. 17 depicts CTGF and its recovery in normal urine. Four aliquots were spiked with a different amount of CTGF, and a fifth served as a control. Immunoblotting was performed using a CTGF specific antibody.

FIG. 18 depicts the analysis of CTGF protein in urine of diseased patients or healthy volunteers. Urine samples from 8 patients with kidney disease or 3 normal volunteers were assayed for CTGF by immunoblotting.

DETAILED DESCRIPTION OF THE INVENTION

It is understood that the present invention is not limited to the particular methodologies, protocols, cell lines, and reagents, etc., described herein, as these may vary. It is also to be understood that the terminology used herein is used for the purpose of describing particular embodiments only, and is not intended to limit the scope of the present invention. It must be noted that as used herein and in the claims, the singular forms "a", "an", and "the" include plural references unless the context clearly dictates otherwise. Thus, for example, a reference to "an antibody" is a reference to one or more antibodies and any equivalents thereof known to those skilled in the art.

Unless defined otherwise, all technical and scientific terms used herein have the same meanings as commonly understood by one of ordinary skill in the art to which this invention belongs. Preferred methods, devices, and materials are described, although any similar or equivalent methods can be used in the practice or testing of the present invention. All patents, publications, and other references cited herein are incorporated by reference herein in their entirety.

Definitions

As used herein, the term "extracellular matrix" refers broadly to non-cellular matrix, typically composed of proteins, glycoproteins, complex carbohydrates, and other macromolecules. Extracellular matrix components include, for example, collagen types I and IV, fibronectin, laminin, and thrombospondin.

The term "fibrosis" refers to abnormal processing of fibrous tissue, or fibroid or fibrous degeneration. Fibrosis can result from various injuries or diseases, and can often result from chronic transplant rejection relating to the transplantation of various organs. Fibrosis typically involves the abnormal production, accumulation, or deposition of extracellular matrix components, including overproduction and increased deposition of, for example, collagen and fibronectin.

As used herein, the terms "kidney fibrosis" or "renal fibrosis" or "fibrosis of the kidney" refer to diseases or disorders associated with the overproduction or abnormal deposition of extracellular matrix components, particularly collagen, leading to the degradation or impairment of kidney function. The terms "disorders" and "diseases" are used inclusively and refer to any condition deviating from normal. "Diseases" and "disorders" include, but are not limited to, allograft and transplant rejection, acute and chronic, and any transplant nephropathy; acute and chronic kidney failure; autoimmune nephropathy; diabetic nephropathy; glomerulonephritis, glomerulosclerosis, and other forms of glomerular abnormality or injury; hypertension; hypertrophy; interstitial disease; nephritis; sclerosis, an induration or hardening of tissues and/or vessels resulting from causes that include, for example, inflammation due to disease or injury; renal-associated proliferative disorders; and other primary or secondary nephrogenic conditions. Fibrosis associated with dialysis following kidney failure and catheter placement, e.g., peritoneal and vascular access fibrosis, is also included.

It is understood that, while kidney fibrosis is the model for discussion of the present invention, the mechanism of fibrosis is universal. Therefore, the presently described methods, kits, and other aspects of the present invention could also be directed to the diagnosis, prevention, and treatment of other forms of fibrosis and diseases and disorders associated with fibrosis and proliferation, including, but not limited to: cardiac fibrosis, pulmonary fibrosis, diabetic retinopathy, skin fibrosis, scleroderma, atherosclerosis, arteriosclerosis, hypertropic scarring, keloid formation, arthritis, liver fibrosis, inflammation, tumor growth metastasis, other conditions related to cell proliferation and migration, including those associated with vascular endothelial cells, for example, angiogenesis and neovascularization, etc.

The term "sample" is used herein in its broadest sense. Samples may be derived from any source, for example, from bodily fluids, secretions, or tissues including, but not limited to, saliva, blood, urine, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. A sample can be in solution or can be, for example, fixed or bound to a substrate. A sample can refer to any material suitable for testing for the presence of CTGF or suitable for screening for molecules that bind to CTGF or fragments thereof. Methods for obtaining such samples are within the level of skill in the art.

An "antisense sequence" is any sequence capable of specifically hybridizing to a target sequence. The antisense sequence can be DNA, RNA, or any nucleic acid mimic or analog. The term "antisense technology" refers to any technology which relies on the specific hybridization of an antisense sequence to a target sequence.

The terms "modulation" and "regulation" as used with respect to CTGF expression or activity refer to any direction of or effect on CTGF expression or activity as compared to normal or to unaltered CTGF expression or activity.

Invention

A. CTGF and its Role in Fibrosis and Renal Disorders

The present invention is based on the discovery that CTGF is an important mediator of extracellular accumulation in fibrotic conditions, and, in particular, in fibrotic conditions associated with renal disorders, such as diabetes and glomerular hypertension. More specifically, the present invention is based on the discovery that the production of CTGF by glomerular cells (in particular, mesangial cells) is a potentially important factor in the pathogenesis of diseases and disorders of the kidney. It was discovered that increased levels of CTGF induced increased production and deposition of ECM in mesangial cells. It was further found in an analysis of urine samples that healthy subjects had no or very minimal levels of CTGF in their urine, while the urine of diabetic patients or patients with other renal disorders showed increased levels of CTGF.

To demonstrate that CTGF is a critical determinant of extracellular matrix deposition in the kidney, CTGF expression in mesangial cells, glomeruli, and whole kidney was examined under diabetic and non-diabetic conditions. Mesangial cells cultured in media containing normal levels of glucose expressed low levels of CTGF mRNA and secreted barely detectable amounts of the full length CTGF protein. However, in a hyperglycemic environment in which mesangial cells were exposed to elevated glucose levels, upregulation of CTGF expression and increased protein production were detected. Moreover, mechanical strain of mesangial cells, exhibitive of, for example, glomerulosclerosis, glomerular hypertension, and glomerular hypertrophy, demonstrated an upregulated expression and protein production of CTGF in mesangial cells. Thus, the present invention demonstrates that exposure to conditions such as increased glucose concentrations, mechanical force, or TGF-$\beta$ led to upregulated expression and protein production of CTGF, establishing a nexus between the presence of CTGF and renal disorders, in particular, diabetes and hypertension. Even in the absence of hypertension, conditions that produce, for example, glomerular hypertrophy, often a result of renal injury, can result in induce increased capillary vessel diameter. According to Laplace's law, vessel wall tension is correspondingly increased, and increased mesangial cell stretching forces are likely produced. See Cortes et al., 1997, supra.

B. Methods for Modulating and Inhibiting Activity of CTGF

Connective Tissue Growth Factor (CTGF) is a critical determinant of extracellular matrix deposition in kidney fibrotic conditions. The present invention provides methods for the diagnosis, prevention, and treatment of complications associated with kidney fibrosis, preferably, by regulating, modulating, and/or inhibiting the expression or activity of CTGF. More specifically, methods of the present invention provide for the administration of a therapeutically effective amount of an agent that regulates, modulates, and/or inhibits the extracellular matrix producing activity of CTGF.

Antibodies. In one embodiment of the present invention, methods for diagnosis, prevention, and treatment of renal disorders and diseases involve the administration of a therapeutically effective amount of an antibody which specifically reacts with a CTGF polypeptide or fragments thereof.

CTGF antibodies may be generated using methods well known in the art. Such antibodies may include, but are not limited to, polyclonal, monoclonal, chimeric, single chain antibodies, as well as Fab fragments, including $F(ab')_2$ and $F_v$ fragments. Fragments can be produced, for example, by a Fab expression library. Neutralizing antibodies, i.e., those which inhibit dimer formation, are especially preferred for therapeutic use.

A target polypeptide, such as CTGF or an agent that modulates the activity and or expression of CTGF, can be evaluated to determine regions of high immunogenicity. Methods of analysis and epitope selection are well known in the art. See, e.g., Ausubel et al., eds., 1988, *Current Protocols in Molecular Biology*, John Wiley & Sons, Inc., New York N.Y. Analysis and selection can also be accomplished, for example, by various software packages, such as LASERGENE NAVIGATOR software. (DNASTAR; Madison Wis.) The peptides or fragments used to induce antibodies should be antigenic, but are not necessarily biologically active. Preferably, an antigenic fragment or peptide is at least 5 amino acids in length, more preferably, at least 10 amino acids in length, and most preferably, at least 15 amino acids in length. It is preferable that the antibody-inducing fragment or peptide is identical to at least a portion of the amino acid sequence of the target polypeptide, e.g., CTGF. A peptide or fragment that mimics at least a portion of the sequence of the naturally occurring target polypeptide can also be fused with another protein, e.g., keyhole limpet hemocyanin (KLH), and antibodies can be produced against the chimeric molecule.

Methods for the production of antibodies are well known in the art. For example, various hosts, including goats, rabbits, rats, mice, humans, and others, may be immunized by injection with the target polypeptide or any immunogenic fragment or peptide thereof. Depending on the host species, various adjuvants may be used to increase immunological response. Such adjuvants include, but are not limited to, Freund's adjuvant, mineral gels such as aluminum hydroxide, and surface-active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

Monoclonal and polycolonal antibodies may be prepared using any technique which provides for the production of antibody molecules by continuous cell lines in culture. Techniques for in vivo and in vitro production are well known in the art. See, e.g., Pound, 1998, *Immunochemical Protocols*, Humana Press, Totowa N.J.; Harlow and Lane, 1988, *Antibodies, A Laboratory Manual*, Cold Spring Harbor Laboratory, New York N.Y. The production of chimeric antibodies is also well known, as is the production of single-chain antibodies. See, e.g., Morrison et al., 1984, *Proc Natl Acad Sci* 81:6851-6855; Neuberger et al., 1984, *Nature* 312:604-608; Takeda et al., 1985, *Nature* 314:452-454. Antibodies with related specificity, but of distinct idiotypic composition, may be generated, for example, by chain shuffling from random combinatorial immunoglobin libraries. See, e.g., Burton, 1991, *Proc Natl Acad Sci* 88:11120-11123.

Antibodies may also be produced by inducing in vivo production in the lymphocyte population or by screening immunoglobulin libraries or panels of highly specific binding reagents. See, e.g., Orlandi et al., 1989, *Proc Natl Acad Sci* 86:3833-3837; Winter and Milstein, 1991, *Nature* 349:293-299). Antibody fragments which contain specific binding sites for the target polypeptide may also be generated. Such antibody fragments include, but are not limited to, $F(ab')_2$ fragments, which can be produced by pepsin digestion of the antibody molecule, and Fab fragments, which can be generated by reducing the disulfide bridges of the $F(ab')2$ fragments. Alternatively, Fab expression libraries may be constructed to allow rapid and easy identification of monoclonal Fab fragments with the desired specificity. See, e.g., Huse et al., 1989, *Science* 254:1275-1281.

Antibodies can be tested for anti-target polypeptide activity using a variety of methods well known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art. See, e.g., Harlow and Lane. Such immunoassays typically involve the measurement of complex formation between the target polypeptide and a specific antibody. A two-site, monoclonal-based immunoassay utilizing monoclonal antibodies reactive to two non-interfering epitopes on the target polypeptide is preferred, but other assays, such as a competitive binding assay, may also be employed. See, e.g., Maddox et al, 1983, *J Exp Med* 158: 1211.

Antibodies as described above could also be used to identify CTGF or fragments thereof in tissue, e.g., from a kidney biopsy. The amount of CTGF present could be determined, for example, by quantitative image analysis. CTGF mRNA levels could also be determined, such as by reverse transcriptase polymerase chain reaction (PCR) using portions of the biopsied tissue, e.g., glomeruli. In particular, in this method, mRNA from a tissue sample, in total, or that specific for CTGF or fragments thereof, could be transcribed to DNA and then amplified through PCR using CTGF-specific primer sequences. Quantitation of mRNA for CTGF or fragments thereof could be determined, for example, by a competition reaction using equal volumes of the patient sample run against a series of decreasing known concentrations, e.g., of a mimic or mutant cDNA fragment.

The present invention contemplates the use of antibodies specifically reactive with a CTGF polypeptide or fragments thereof which neutralize the biological activity of CTGF. The antibody administered in the method can be the intact antibody or antigen binding fragments thereof, such as Fab, $F(ab')_2$, and $F_v$ fragments, which are capable of binding the epitopic determinant. The antibodies used in the method can be polyclonal or, more preferably, monoclonal antibodies. Monoclonal antibodies with different epitopic specificities are made from antigen containing fragments of the protein by methods well known in the art. See, e.g., Kohler et al., 1975, *Nature* 256:495-497; Ausubel, et al., supra.

In the present invention, therapeutic applications include those using "human" or "humanized" antibodies directed to CTGF or fragments thereof. Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a CTGF is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

In another embodiment of the present invention, a method involves the administration of a therapeutically effective amount of an antibody reactive to a CTGF responsive receptor, and, more specifically, an antibody which blocks the binding of CTGF to its cellular receptors. The method of the present invention provides that the antibody reactive with CTGF modulates and/or inhibits the biological activity of CTGF through the manipulation and control of the interaction between CTGF and its receptor by inactivation of the receptor independently of CTGF.

Antisense Oligonucleotides. The present invention provides for a therapeutic approach which directly interferes with CTGF expression. Specifically, a therapeutic approach which directly interrupts the translation of CTGF mRNA into protein could be used to bind to CTGF mRNA or to otherwise interfere with CTGF expression. Antisense technology relies on the modulation of expression of a target protein through the specific binding of an antisense sequence to a target sequence encoding the target protein or directing its expression. See, e.g., Agrawal, ed., 1996, *Antisense Therapeutics*, Humana Press, Inc., Totowa N.J.; Alama et al., 1997, *Pharmacol Res* 36(3):171-178; Crooke, 1997, *Adv Pharmacol* 40:1-449; and Lavrosky et al., 1997, *Biochem Mol Med* 62(1): 11-22. Antisense sequences are nucleic acid sequences capable of specifically hybridizing to at least a portion of a target sequence. Antisense sequences can bind to cellular mRNA or genomic DNA, blocking translation or transcription and thus interfering with expression of a targeted protein product. Antisense sequences can be any nucleic acid material, including DNA, RNA, or any nucleic acid mimics or analogs. See, e.g., Rossi et al., 1991 *Antisense Res Dev* 1(3): 285-288; Pardridge et al., 1995, *Proc Natl Acad Sci* 92(12): 5592-5596; Nielsen and Haaima, 1997, *Chem Soc Rev* 96:73-78; and Lee et al., 1998, *Biochemistry* 37(3):900-1010. Delivery of antisense sequences can be accomplished in a variety of ways, such as through intracellular delivery using an expression vector. See discussion, infra. Site-specific delivery of exogenous genes is also contemplated, such as techniques in which cells are first transfected in culture and stable transfectants are subsequently delivered to the target site. See, e.g., Kitamura et al., 1994, *Kidney Int* 43:S55-S58.

Antisense oligonucleotides of about 15 to 25 nucleic acid bases are typically preferred as such are easily synthesized and are capable of producing the desired inhibitory effect. Molecular analogs of antisense oligonucleotide may also be used for this purpose and can have added advantages such as stability, distribution, or limited toxicity advantageous in a pharmaceutical product. In addition, chemically reactive groups, such as iron-linked ethylenediamine-tetraacetic acid (EDTA-Fe), can be attached to antisense oligonucleotides, causing cleavage of the RNA at the site of hybridization. These and other uses of antisense methods to inhibit the in vitro translation of genes are well known in the art. See, e.g., Marcus-Sakura, 1988, *Anal Biochem* 172:289.

Delivery of antisense therapies and the like can be achieved intracellularly through using a recombinant expression vector such as a chimeric virus or a colloidal dispersion system which, upon transcription, produces a sequence complementary to at least a portion of the cellular sequence encoding the target protein. See, e.g., Slater et al., 1998, *J Allergy Clin Immunol* 102(3):469-475. Delivery of antisense sequences can also be achieved through various viral vectors, including retrovirus and adeno-associated virus vectors. See, e.g., Miller, 1990, *Blood* 76:271; and Uckert and Walther, 1994, *Pharacol Ther* 63(3):323-347. Vectors which can be utilized for antisense gene therapy as taught herein include, but are not limited to, adenoviruses, herpes viruses, vaccinia, or, preferably, RNA viruses such as retroviruses.

Retroviral vectors are preferably derivatives of murine or avian retrovirus. Retroviral vectors can be made target-specific by inserting, for example, a polynucleotide encoding a protein or proteins such that the desired ligand is expressed on the surface of the viral vector. Such ligand may be a glycolipid carbohydrate or protein in nature. Preferred targeting may also be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Recombinant retroviruses are typically replication defective, and can require assistance in order to produce infectious vector particles. This assistance can be provided by, for example, using helper cell lines that contain plasmids encoding all-of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal may be used. These cell lines produce empty virions, since no genome is packaged. If a retroviral vector is introduced into such cells in which the packaging signal is intact, but the structural genes are replaced by other genes of interest, the vector can be packaged and vector virion produced.

Other gene delivery mechanisms that can be used for delivery of antisense sequences to target cells include colloidal dispersion and liposome-derived systems, artificial viral envelopes, and other systems available to one of skill in the art. See, e.g., Rossi, 1995, *Br Med Bull* 51(1):217-225; Morris et al., 1997, *Nucleic Acids Res* 25(14):2730-2736; and Boado et al., 1998, *J Pharm Sci* 87(11):1308-1315. For example, delivery systems can make use of macromolecule complexes, nanocapsules, microspheres, beads, and lipid-based systems including oil-in-water emulsions, micelles, mixed micelles, and liposomes.

In one embodiment, a method of the present invention administers a therapeutically effective amount of an antisense oligonucleotide having a sequence capable of binding specifically with any sequences of an mRNA molecule which encodes CTGF, so as to prevent translation of CTGF mRNA.

In another embodiment of the present invention, a method is provided in which a therapeutically effective amount of an antisense oligonucleotide having a sequence capable of binding specifically with any sequences of CTGF mRNA so as to prevent translation of the mRNA.

Small Molecule Inhibitors. The present invention further provides a method in which small molecules are used to inhibit the activity of CTGF by blocking the binding of responsive cytokines to the CTGF responsive receptor. For example, the present invention provides methods of treating and preventing kidney fibrosis utilizing small molecules that modulate, regulate and inhibit CTGF activity.

In order to identify small molecules and other agents useful in the present methods for treating or preventing a renal disorder by modulating the activity and expression of CTGF, CTGF and biologically active fragments thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between CTGF and the agent being tested can be measured by methods available in the art.

Other techniques for drug screening which provide for a high throughput screening of compounds having suitable binding affinity to CTGF, or to another target polypeptide useful in modulating, regulating, or inhibiting the expression and/or activity of CTGF, are known in the art. For example, microarrays carrying test compounds can be prepared, used, and analyzed using methods available in the art. See, e.g., Shalon, D. et al., 1995, International Publication No. WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Identifying small molecules that modulate CTGF activity can also be conducted by various other screening techniques, which can also serve to identify antibodies and other compounds that interact with CTGF and can be used as drugs and therapeutics in the present methods. See, e.g., Enna et al., eds., 1998, *Current Protocols in Pharmacology*, John Wiley & Sons, Inc., New York N.Y. Assays will typically provide for detectable signals associated with the binding of the compound to a protein or cellular target. Binding can be detected by, for example, fluorophores, enzyme conjugates, and other detectable labels well known in the art. See, e.g., Enna et al., supra. The results may be qualitative or quantitative.

For screening the compounds for specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody of the galactosyl epitope. Various labels can be used such as radioisotopes, enzymes, fluorescers, chemiluminescers, particles, etc. There are numerous commercially available kits providing labeled anti-hIg, which may be employed in accordance with the manufacturer's protocol.

For screening the compounds for cytotoxic effects, a wide variety of protocols may be employed to ensure that one has the desired activity. One will normally use cells, which may be naturally occurring or modified, cell lines, or the like. The cells may be prokaryotic or eukaryotic. For example, if one is interested in a pathogen, where it does not matter to which epitope the compound conjugate binds, one can combine the pathogenic cells with each of the compounds in the presence of an antibody dependent cytotoxic system to determine the cytotoxic effect. One may perform this assay either prior to or subsequent to determining the effect of the various candidate compounds on cells of the host to whom the compound would be administered. In this way, one would obtain a differential analysis between the affinity for the pathogenic target and the affinity for host cells which might be encountered, based on the mode of administration.

In some situations, one would be interested in a particular cellular status, such as an activated state, as may be present with T cells in autoimmune diseases, transplantation, and the like. In this situation one would first screen the compounds to determine those which bind to the quiescent cell, and as to those compounds which are not binding to the quiescent cells, and screen the remaining candidate compounds for cytotoxicity to the activated cells. One may then screen for other cells present in the host which might be encountered by the compounds to determine their cytotoxic effect. Alternatively, one might employ cancer cells and normal cells to determine whether any of the compounds have higher affinity for the cancer cells, as compared to the normal cells. Again, one could screen the library of compounds for binding to normal cells and determine the effect. Those compounds which are not cytotoxic to normal cells could then be screened for their cytotoxic effect to cancer cells. Even where some cytotoxicity exists for normal cells, in the case of cancer cells, where there is a sufficient differentiation in cytotoxic activity, one might be willing to tolerate the lower cytotoxicity for normal cells, where the compound is otherwise shown to be effective with cancer cells.

Instead of using cells which are obtained naturally, one may use cells which have been modified by recombinant techniques. Thus, one may employ cells which can be grown in culture, which can be modified by upregulating or downregulating a particular gene. In this way, one would have cells that differ as to a single protein on the surface. One could then differentially assay the library as to the effect of members of the library on cells for which the particular protein is present or absent. In this way, one could determine whether the compound has specific affinity for a particular surface membrane protein as distinct from any of the proteins present on the surface membrane.

One may differentiate between cells by using antibodies binding to a particular surface membrane protein, where the antibodies do not initiate the complement dependent cytotoxic effect, for example, using different species, isotypes, or combinations thereof. By adding the antibodies, blocking antisera or monoclonal antibodies, to one portion of the cells, those cells will not have the target protein available for binding to the library member. In this way one creates comparative cells which differ in their response based on the unavailability in one group of a single protein. While antibodies will usually be the most convenient reagent to use, other specific binding entities may be employed which provide the same function.

For use in the assay to determine binding, one may use an antibody-dependent cytotoxic system. One could use synthetic mixtures of the ingredients, where only those components necessary for the cytotoxic effect are present. This may be desirable where components of blood or plasma may adversely affect the results of the assay.

Also, while a cellular lawn is an extremely convenient way to screen large numbers of candidates, other techniques may also find use. These techniques include the use of multiwell plates, and the various devices used for the preparation of the combinatorial library, such as pins, tea bags, etc. One may grow the cells separately in relation to the nature of the various devices, where the device may then be contacted with the cells or have the cells grown on the device. The device may be immersed in an appropriate culture, seeded with the cells, or otherwise provided for contact between the cells and the candidate compound. After adding the cytotoxic agent, one may then analyze for lysis in a variety of ways. For example, FACS may be used for distinguishing between live and dead cells, [$^{51}$Cr] release may be employed, or detection of an intracellular compound in the supernatant, may serve to detect active compounds.

In addition, one may wish to know whether the compound has agonist or antagonist activity. The subject assay techniques provide for a rapid way for determining those compounds present in the library which bind to the target protein. Once, one has substantially narrowed the number of candidate compounds, one can use more sophisticated assays for detecting the activity of the compound itself. In this way, one can perform a rapid screen to determine binding affinity and specificity, followed by a more intensive screen to determine activity. Various techniques exist for determining activity, where the cells may be modified, so that a marker gene will be activated which will provide for a detectable signal. Conveniently, the signal may be associated with production of a dye, the production of a surface membrane protein which can be detected with labeled antibodies, or the secretion of a protein which can be detected in the supernatant by any of a variety of techniques. For example, the gene that is expressed may be luciferase modified to have a leader sequence so as to be secreted, whereby the supernatant can then be screened for light generation formation by using an appropriate substrate.

Various protocols may be employed for screening the library. To some degree, this will depend upon the nature of the preparation of the compounds. For example, the compounds may be bound to individual particles, pins, membranes, or the like, where each of the compounds is segregatable. In addition, the amount of compound available will vary, depending upon the method employed for creating the library. Furthermore, depending upon the nature of the attachment of the compound to the support, one may be able to release aliquots of a compound, so as to carry out a series of assays. In addition, the manner in which the compounds are assayed will be affected by the ability to identify the compound which is shown to have activity.

Where the compounds are individually on a surface in a grid, so that at each site of the grid one knows what the composition is, one can provide a cellular lawn which is similarly organized as a grid and may be placed in registry with the compounds bound to the solid surface. Once the lawn and solid substrate are in registry, one may release the compounds from the surface in accordance with the manner in which the compounds are attached. After sufficient time for the compounds to bind to the proteins on the cellular surface, one may wash the cellular lawn to remove non-specifically bound compounds. One or more washings may be involved, where the washings may provide for varying degrees of stringency, depending upon the desired degree of affinity. After the washings have been completed, mammalian blood or plasma may then be added and incubated for sufficient time for cytotoxicity. The plasma or blood may then be removed and plaques observed, where the nature of the compound can be determined by virtue of the position in the grid. The plasma or blood can be free of any components that would naturally kill the cells of the lawn.

Since the preparative process may be repeated, one could prepare a plurality of solid substrates, where the same compounds are prepared at the comparable sites, so that the screening could be repeated with the same or different cells to determine the activity of the individual compounds. In some instances, the identity of the compound can be determined by a nucleic acid tag, using the polymerase chain reaction for amplification of the tag. See, e.g., International Publication No. WO93/20242. In this instance, the compounds that are active may be determined by taking the lysate and introducing the lysate into a polymerase chain reaction medium comprising primers specific for the nucleic acid tag. Upon expansion, one can sequence the nucleic acid tag or determine its sequence by other means, which will direct the selection of the procedure that is used to prepare the compound.

Alternatively, one may have tagged particles where the tags are releasable from the particle and provide a binary code that describes the synthetic procedure for the compounds bound to the particle. See, e.g., Ohlmeyer et al., 1993, *Proc Natl Acad Sci USA* 90:10922. These tags can conveniently be a homologous series of alkylene compounds, which can be detected by gas chromatography-electron capture. Depending upon the nature of the linking group, one may provide for partial release from the particles, so that the particles may be used 2 or 3 times before identifying the particular compound.

While for the most part libraries have been discussed, any large group of compounds can be screened analogously, so long as the CTGF epitope can be joined to each of the compounds. Thus, compounds from different sources, both natural and synthetic, including macrolides, oligopeptides, ribonucleic acids, dendrimers, etc., may also be screened in an analogous manner.

Formation of a plaque in the assay demonstrates that binding of the member of the library to the cell, usually a surface protein, does not interfere with the CTGF epitope binding to an antibody, that the immune complex is sufficiently stable to initiate the complement cascade, and that the member has a high affinity for the target.

The subject methodology can be used in any situation where one has a cellular target to be killed, particularly those cellular targets having low or no CTGF epitope. Thus, the cellular target may be a prokaryote, which is pathogenic. Various organisms include, for example, microbacterium, *Yersinia, Pseudomonas, Bordetella pertussis, Treponema pallidum, Neisseria gonorrhoea, Streptococcus, Hemophilus influenza*, etc. Other pathogens include eukaryotes, particularly fungi, such as *Candida, Histoplasma*, etc., and protozoa, e.g., *Giardia*. In addition, viruses which provide for surface membrane proteins in infected cells, can also be the target of the subject compounds, where the cells that are screened have been vitally infected.

Host cells may also serve as targets, where the cells are either abnormal or act in an adverse way to the host or treatments of the host. For example, cancerous tissues which can be distinguished from normal tissue can serve as a target for the subject compounds. T or B cells associated with autoimmune diseases or associated with GVHD or transplant rejection may also serve as targets. Aberrant cells, regardless of their nature, so long as they can be distinguished from normal cells, may also serve as targets. Thus, psoriatic lesions, lymphoma cells, bacterial, fungal, parasitic, virus infected cells, may be targets of the subject products. Also, where one wishes to ablate a portion of cells, without removal of all of the cells, such as cells expressing a differentiation marker such as T cell subsets, activated platelets, endothelial cells, hormone or cytokine receptor expressing cells, the subject compounds may find application.

Other screening methods for obtaining small molecules that modulate the activity of CTGF can be found, for example, International Publication No. WO 98/13353.

Compounds/Molecules. The present invention provides methods for treating and preventing disorders associated with kidney fibrosis by modulating, regulating, or inhibiting the activity of CTGF. These methods can comprise the administration of a therapeutically effective amount of a compound that blocks the binding interactions or blocks enzymes involved in the signal transduction pathway of CTGF. More specifically, the present invention provides a method for inhibiting the activity of CTGF by administering compounds that block the induction of CTGF.

Compounds that modulate CTGF gene expression and/or CTGF activity in the method of the invention include agents which cause an elevation in cyclic nucleotides in the cell. Other compounds that may block the induction of CTGF according to the methods of the present invention may be identified using the screening methods described above.

In yet a further embodiment of the present invention, the method provides for the administration of molecules that interrupt the post-translational modification of full length CTGF or block the activation of an inactive precursor of CTGF. As discussed herein, exposure of mesangial cells to TGF-β resulted in the marked appearance of additional bands at 28-30 kDa which correspond in size to the carboxy- and amino-terminal halves of the full length CTGF molecule. As disclosed above, TGF-β treatment may result in the production of proteases or other factors capable of cleaving the full-length molecule. Molecules that inhibit CTGF activity may be identified using the screening methods provided herein.

The methods of the present invention may further be used to prevent or treat fibrosis in the kidney associated with allograft rejection comprising administering a therapeutically effective amount of any one of the agents described above.

The invention further provides a method for treating or preventing diabetes by administering an effective amount of insulin and an effective amount of an agent that regulates, modulates, or inhibits CTGF activity as described above.

C. Pharmaceutical Formulations and Routes of Administration

Routes of Administration. The antibodies, small molecules, and other compounds described herein can be administered to a human patient per se, or in pharmaceutical compositions comprising, where appropriate, suitable carriers or excipients. The present invention contemplates methods of treatment in which agents that modulate or regulate the expression or activity of CTGF or fragments thereof are administered to a patient in need, in amounts suitable to treat or prevent the overproduction of ECM associated with CTGF. The present methods of treatment and prevention can comprise administration of an effective amount of the agent to a subject which is preferably a mammalian subject, and most preferably a human subject. In a preferred embodiment, the subject mammal and the agent administered are of homologous origin. Most preferably, the subject and the agent administered are human in origin.

An effective amount can readily be determined by routine experiment, as can the most effective and convenient route of administration and the most appropriate formulation. Various formulations and drug delivery systems are available in the art. See, e.g., Gennaro, ed., 1990, *Remington's Pharmaceutical Sciences*, 18$^{th}$ ed., Mack Publishing Co., Easton Pa. Suitable routes of administration may, for example, include oral, rectal, transmucosal, or intestinal administration and parenteral delivery, including intramuscular, subcutaneous, intramedullary injections, as well as intrathecal, direct intraventricular, intravenous, intraperitoneal, intranasal, or intraocular injections. The composition may be administered in a local rather than a systemic manner. For example, a composition comprising an agent which modulates, regulates, or inhibits the activity of CTGF can be delivered via injection or in a targeted drug delivery system into an area in which there is excess circulating CTGF or ECM overproduction or into an area in which inhibition of CTGF activity is desired, often in a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping or lyophilizing processes. As noted above, the compositions of the present invention can include one or more physiologically acceptable carriers such as excipients and auxiliaries which facilitate processing of active molecules into preparations for pharmaceutical use. Proper formulation is dependent upon the route of administration chosen.

For injection, for example, the composition may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of agents that affect the activity of CTGF or fragments thereof, in water-soluble form.

Suspensions of the active compounds may be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

The compositions of the present invention may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical carriers for the hydrophobic molecules of the invention could include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Effective Dosage. For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Where inhibition of CTGF activity is desired, for example, the concentration of the test compound which achieves a half-maximal inhibition of CTGF activity can be determined. Dosage ranges appropriate for human subjects can be determined using data obtained from cell culture assays and other animal studies.

A therapeutically effective dose refers to that amount of the molecule that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Molecules which exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage will be chosen in view of the specifics of a subject's condition.

Dosage amount and interval may be adjusted individually to provide plasma levels of the active moiety which are sufficient to modulate or regulate CTGF activity as desired, i.e. minimal effective concentration (MEC). The MEC will vary for each compound but can be estimated from, for example, in vitro data, such as the concentration necessary to achieve 50-90% activity of CTGF to induce bone growth using the assays described herein.

Dosages necessary to achieve the MEC will depend on individual characteristics and route of administration. Compositions should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of composition administered will, of course, be dependent on a number of factors, including, but not limited to, the particular subject's weight, the severity of the affliction, the manner of administration, and the judgment of the prescribing physician.

Packaging. The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of disorders or diseases in which cartilage or bone induction, wound healing, neuroprotection or the like is desired.

Receptor-Ligand Complexes. As a consequence of the above described screening techniques, as well as other known screening techniques which may be applied in the context of the present invention, CTGF-ligand complexes can be formed. These complexes may include complexes wherein the ligand is a CTGF antagonist, a CTGF agonist, or any another compound capable of modulating the expression and activity of CTGF. Partial agonists or antagonists of the CTGF receptor may be useful for therapeutic or diagnostic purposes. CTGF-agent complexes may be useful as therapeutic entities in their own right or in methods of detecting and quantifying CTGF levels in a sample. The measurement and quantification of CTGF, for example, through the detection of CTGF-ligand complexes, can be accomplished by methods available in the art. See, e.g., Enna et al., supra.

D. Diagnostics

The present invention is further directed to a method of detecting or diagnosing the presence of pathology of a tissue characterized by an excessive accumulation of the extracellular matrix components, in particular, those associated with renal disorders. One method involves the detection or diagnosis of diabetes, including diabetic nephropathy and diabetic glomerulosclerosis. In a preferred method, the detection or diagnosis is accomplished by measuring CTGF levels in a urine sample from a patient. In one embodiment, the method includes determining the level of CTGF in a first urine sample and comparing this level to the level of CTGF present in a normal urine sample, i.e., a sample from a subject without a renal disorder. An elevated level of CTGF in the first sample is indicative of the pathological condition in question, for example, diabetes or hypertension. In particular, individuals without any renal disorders, normal levels of CTGF may be at or close to zero. In diabetic patients or in patients experiencing infection or other trauma, levels of CTGF may be significantly increased. Thus, the presence of kidney fibrosis could be identified by detecting increases in levels of CTGF in a sample. In a preferred method, the sample is a non-intrusive sample such as a urine sample. Assessment of CTGF levels in a urine sample can be accomplished, for example, by ELISA using a CTGF-specific antibody. Detection of CTGF levels could be indicative of the advancement or worsening of diabetic hypertension or other renal disorders prior to the onset of renal complications, providing for a method of early-stage detection and diagnosis. Furthermore, CTGF levels can serve as a predictor of, for example, which diabetic patients have a predisposition to develop kidney diseases and disorders.

More generally, detection of CTGF levels, including levels of unique forms or fragments of CTGF, may be obtained through immunoassay methods, for example, ELISAs, RIAs, or any other assays which utilize an antibody to detect the presence of a protein marker. The ELISA and RIA methods are preferred and may be used, for example, with the monoclonal antibodies of the present invention to detect levels of CTGF. In a preferred method of the invention, urine samples are obtained first from patients suspected or known to have a renal disease or disorder. Levels of CTGF in this first sample are measured, for example, through immunoassay, and are compared with the CTGF levels in a second sample, the second sample being obtained from a patient known to have a renal disorder or from a patient known not to have any renal disorder, to determine the presence or progression of a kidney disease. The same methods may be used to monitor the progression of a kidney disease.

More generally, antibodies specific for a target polypeptide, such as antibodies specific for CTGF, are useful in the present invention for diagnosis of renal disorders and diseases associated with aberrant expression of CTGF. Diagnostic assays for CTGF can include methods utilizing the antibody and a label to detect CTGF in a sample from a patient suspected of having a renal disorder or disease. The sample could comprise, for example, body fluids, cells, tissues, or extracts of such tissues, including, for example, glomeruli microdissected from biopsy material. Protocols employed to screen for and identify antibodies having the desired specificity can also be used for the detection of CTGF or the target polypeptide in the sample.

Preferably, in the diagnostic methods of the present invention, normal or standard values for CTGF expression are established in order to provide a basis for the diagnosis of the existence of a renal disease or disorder or a predisposition to a renal disease or disorder. In one of the methods of the present invention, this is accomplished by combining body fluids or cell extracts taken from normal subjects with antibody to CTGF under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified CTGF. Standard values obtained from normal samples may be compared, for example, in a specific embodiment, with values obtained from samples from subjects suspected of having a kidney disease or disorder, or having a predisposition to a kidney disease or disorder, associated with kidney fibrosis. Deviation between standard and subject values establishes the presence of or predisposition to the disease state. The diagnostic methods of the present invention may also be directed to the detection of a predisposition or susceptibility to a renal disorder. This can be accomplished, for example, by detecting a marker indicative of a predisposition or susceptibility to develop a particular disorder, for example, diabetes. The marker can comprise, for example, a genetic polymorphism.

Monoclonal antibodies can be detected by methods discussed, for example, supra. Monoclonal antibodies against CTGF can be conjugated to an appropriate enzyme such as horseradish peroxidase, protein ferritin, enzyme alkaline phosphatase, β-D-galactosidase etc. These enzyme-linked antibody preparations can be mixed with, for example, urine samples that contain unknown amounts of CTGF in an indirect ELISA. Direct or sandwich ELISAs could also be performed using the same antibodies.

RIA techniques may also be used to measure levels of CTGF in, for example, urine. For example, CTGF may be radioactively labeled and mixed with monoclonal antibodies specific for CTGF and a serum sample containing an unknown amount of unlabeled CTGF. Binding competition between the labeled and unlabeled CTGF with the monoclonal antibody occurs. By measuring the amount of radioactivity of the reaction mixture, the amount of CTGF present in the sample can be quantitatively determined. See, e.g., U.S. Pat. Nos. 4,438,209 and 4,591,573. Non-competitive RIAs can also be performed.

Polynucleotide sequences encoding CTGF can be used for the diagnosis of conditions or diseases associated with increased levels of CTGF expression. For example, polynucleotide sequences encoding CTGF may be used in hybridization or PCR assays of fluids or tissues from biopsies to detect CTGF expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The present invention additionally provides methods for evaluating the effectiveness of anti-fibrotic therapy, including the use of ACE inhibitors, by measuring the levels of CTGF in a sample from a subject undergoing a course of treatment for diseases and disorders associated with fibrosis. CTGF levels can be measured in samples, for example, urine sample, taken from the subject at various points before, during, and after a course of treatment. The efficacy of a treatment can be evaluated with reference to the variation in CTGF levels present in the samples taken at different stages of a course of treatment.

Kits. The present invention provides kits for detecting CTGF in samples, in particular, in fluid samples. In a preferred embodiment, the diagnostic kits of the present invention contain reagents for measuring levels of CTGF in urine samples. In a particular embodiment, this kit comprises a monoclonal antibody specific for CTGF bound to a support and a second monoclonal antibody specific for a different CTGF epitope and enzyme-labeled. The kit further comprises reagents for detecting the enzyme-labeled monoclonal antibody. The reagent kit employs immunological methods in measuring CTGF in the urine sample, thus allowing for the detection and monitoring of kidney disorders and diseases. In particular embodiments, the kit allows for the detection and monitoring of fibrotic and sclerotic disorders resulting from, for example, diabetes and hypertension. In another embodiment, the kit comprises a radio-labeled or fluorescein-labeled antibody in place of the enzyme-labeled antibody.

In one embodiment, the diagnostic kit of the present invention comprises elements useful in the detection of CTGF in tissue samples, using immunohistochemical techniques. The kit could be used in conjunction with, for example, a software program which allows for quantitative measurement of the levels of CTGF in the tissue sample by image analysis or other comparative techniques. See, e.g., Riser et al., 1996, supra. Another embodiment provides a diagnostic kit for detecting and measuring levels of CTGF mRNA in tissue samples. In one embodiment, the kit comprises reagents used to reverse transcribe CTGF mRNA to DNA. The kit can further comprise reagents necessary to amplify CTGF-specific DNA, including primers complementary to polynucleotides encoding CTGF or fragments thereof. The kit can also include a competitive mimic or mutant cDNA for use in quantifying the level of CTGF mRNA present in the sample.

In a preferred embodiment, the diagnostic kit of the present invention is packaged and labeled, for example, in box or container which includes the necessary elements of the kit, and includes directions and instructions on the use of the diagnostic kit.

The following examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Unless otherwise stated, the following materials and methods were used in the examples of the present invention.

Cells And Tissue Culture. The mesangial cells were a cloned-line derived from outgrowths of Fischer rat glomeruli, and upon serial passage, these mesangial cells continue to express key markers. (See, e.g., Riser et al., 1998, *J Am Soc Nephrol* 9:827-836.) The medium used was RPMI 1640 with penicillin and streptomycin and, unless otherwise noted, 5 mM glucose. The growth medium contained 20% NU-SERUM media supplement (Collaborative Research, Bedford Mass.). Unless otherwise noted, mesangial cells were cultured for approximately 4 days in growth medium, and when reaching confluency, were washed twice with serum-free medium and incubated for 2448 hours under serum-deprived of 0.5% FCS (fetal calf serum) conditions. The cultures were then incubated for a designated period in fresh maintenance medium (0.5% FCS), with or without experimental treatments. At the concentration of FCS used in these studies, no active TGF-$\beta$1, TGF-$\beta$2, or TGF-$\beta$3 was detectable in the fresh medium, as determined by a highly sensitive mink lung bioassay. (See, e.g., Riser et al., 1996, supra.) The renal fibroblasts used in Northern analysis were mouse tubulointerstitial fibroblasts (TFB). (See, e.g., Alverez, et al., 1998, *Kidney Int* 41:14-23.)

Animals And Specimen Collection. Diabetic male db/db mice and their nondiabetic db/m littermates were obtained from Jackson Laboratories (Bar Harbor Me.). The db/db mouse carries a defective receptor gene for leptin, a key weight control hormone. (See, e.g., Hummel et al., 1966, *Science* 153:1127-1128.) These mice become obese at 3 to 4 weeks of age and develop hyperglycemia. Associated nephropathy includes proteinuria and mesangial expansion with increased mesangial matrix that develops by 5 to 7 months. (See, e.g., Cohen et al., 1995, *J Clin Invest* 95:2338-2345.) In the present experiments, mice were sacrificed at the age of 5 months. Blood glucose levels were determined during the study and at sacrifice, using a colorimetric method based on the glucose oxidase-peroxidase reaction and supplied in a kit form (Glucose Procedure No. 510 kit, Sigma Diagnostics, St. Louis Mo.). Following a 24 hour acclimation to metabolic cages, two consecutive 24 hour urine samples were collected. At the end of the collection period, the lower part of the cage including the collection funnel was rinsed with distilled water and the final sample volume recorded. Protein concentration in the urine was measured according to a method for quantifying microgram quantities of protein utilizing protein-dye binding. (See, e.g., Bradford, 1976, *Anal Biochem* 72:248-254.)

After anesthesia by, an oxygen/ether mixture, the abdominal cavity was opened, a 23 gauge needle was inserted into the aorta and the kidneys were perfused with four (4) ml of ice cold perfusion buffer of (RPMI with 4% BSA) containing 10 mM vanadyl ribonucleoside complex (VRC), an RNase inhibitor (Gibco/BRL, Grand Island, N.Y.). Chilled 0.9% saline was poured over the kidneys during this perfusion. The kidneys were then removed, and the right kidney was frozen in liquid nitrogen for subsequent RNA extraction and Northern analysis. Fine sagittal slices of the left kidney were rapidly obtained. One section was fixed in 3.8% paraformaldehyde, embedded in parafilm and stained with periodic acid Schiff (PAS) for light microscopic evaluation. The remaining slices were used for glomerular microdissection and reverse transcription and polymerase chain reaction (RT-PCR) of the isolated glomeruli. The methods used were a modification of known methods for determining glomerular mRNA levels. (See, e.g., Peten et al., 1993, *Kidney Int Suppl* 39:S55-S58.) Tissue sections were placed in a buffer of HBSS containing 10 mM VRC, and then 50 glomeruli were dissected from each kidney in less than 50 minutes. The glomeruli were next transferred to a PCR tube with 30 µl of rinse buffer (HBSS containing 5 mM DTT and 50 units/ml of human placental ribonuclease inhibitor (Boeringer Mannheim, Indianapolis Ind.). Following centrifugation, the supernatant was removed and microscopically examined for the accidental presence of glomeruli. Seven microliters of a lysis solution (rinse buffer containing 2% Triton X-100) were added, and the samples were stored at −70° C. until processed. All of these procedures were carried out at 4° C.

Experimental samples from control and diabetic mice were thawed on ice and then subjected to 2 additional freeze/thaw cycles to lyse the glomeruli. The RT reaction was then carried out using a cDNA synthesis kit (Boehringer Mannheim), with oligo(dT) as a primer. Reactions containing glomeruli, but without added reverse transcriptase, or without glomeruli, but with reverse transcriptase, served as negative controls. The reaction mixture was incubated for 60 minutes at 42° C., and then chilled to 4° C. for 10 minutes. Samples were then diluted at a ratio of 1:10 in distilled water and frozen at −70° C. until PCR was completed.

Evaluation Of Renal Tissue By Light Microscopy. Five to 6 nonconsecutive 6 µm sections per kidney were PAS stained and examined. Mesangial sclerosis was scored on a scale of zero to four (0-4), wherein zero (0) represents no lesion; one (1) represents minimal mesangial expansion; two (2) represents mesangial expansion and/or basement membrane thickening; three (3) represents marked mesangial thickening, some collapsed lumina, and occasional lobule with full sclerosis; and four (4) represents a diffuse collapse of capillary lumina, and sclerosis involving 75% or more of the tuft. A total of 100-150 glomeruli per kidney were scored by an observer blinded as to the origin of the specimens. Only glomerular profiles showing a mesangial region that could be unequivocally evaluated were scored.

Competitive PCR and Northern blotting. All PCR were performed using the GENEAMP DNA amplification kit (Perkin-Elmer Cetus, Norwalk Conn.) and a 9600 thermal cycler (Perkin Elmer). For quantitation, a competitive PCR reaction was run using a cDNA mimic. Thirty-eight cycles of replication were used. Five PCR tubes were set up for each sample. Each tube in a series contained a fixed amount of the wild-type cDNA along with decreasing concentrations of the mimic cDNA. The products were separated by agarose gel electrophoresis and visualized by ethidium bromide staining. Bands were digitized by scanning densitometry (SCAN-MASTER 3+ densitometer; Howtek, Hudson N.H.) and quantified with image analysis (NIH Image, v. 1.59 from Twilight Clone BBS, Silver Springs Md.). A plot of the ratio of wild type/mimic vs. the reciprocal of the input mutant concentration was constructed and the amount of glomerular cDNA determined from the resulting linear regression. Northern analysis was carried out as previously described, following pulverization of samples in a liquid-nitrogen cooled stainless-steel mortar and homogenization in 1.0 ml of RNA STAT-60 reagent (Tel-Test Inc., Friendswood Tex.). Probes for individual mRNAs and the corresponding cDNAs, were labeled with $^{32}$P by random hexamer priming using the PRIME-1 kit (Sigma). Autoradiograms were digitized by scanning densitometry and quantified as described above.

Primers, probes, and cDNA mimics. Primers for CTGF were designed and synthesized based on conserved sequences between the human and mouse CTGF (fisp 12) gene. The primers, Primer R and Primer F, were as follows: Primer F: 5'-GAG TGG GTG TGT GAC GAG CCC AA G G-3' and Primer R: 5' ATG TCT CCG TAC ATC TTC CTG TAG T-3'. The amplification product was 558 bp in size. The sequence was confirmed by cloning into a PCR script (Invitrogen Corp., Carlsbad Calif.). Two clones were sequenced and were identical. A competitive cDNA mimic was produced using a PCR mimic construction kit (K1700-1, Clontech Laboratories, Palo Alto Calif.). For each mimic, two composite primers (3' and 5') were first made containing the CTGF target gene sequence, plus a 20-nucleotide stretch designed to hybridize to opposite strands of a heterologous DNA fragment provided in the kit. The desired primer sequences were then incorporated into this fragment during PCR amplification. A dilution of the first PCR reaction was then amplified using only the gene-specific primers. This ensured that all mimic molecules had complete gene-specific sequences. The mimic was then purified by passage through CHROMA SPIN TE-100 columns (Clontech). By this method, the size (200-650 bp) could be adjusted by choosing the appropriate sequences of the generic DNA fragment for the composite primers. The resulting cDNA competes on an equal basis for the same primers in the same reaction. An amplimer of the CTGF mimic was 496 bp in size.

Primers (Primer F and Primer R) for rat fibronectin cDNA were Primer F: 5' TGC CAC TGT TCT CCT ACG TG 3' and Primer R: 5'-ATG CTT TGA CCC TTA CAC GG 3'. A competitive mimic for fibronectin was constructed as described above. Products of amplification were approximately 312 bps (sample) and 474 bps (mimic). Primers for GAPDH (Clontech) produced an amplification fragment of 985 bp. A GAPDH competitive mimic was constructed as described above, and produced a fragment of 604 bp. The cDNA probe for Northern analysis was from a sequence of human CTGF shared by rat and mouse.

Production of recombinant CTGF and anti-CTGF antibodies. Recombinant human CTGF protein (rhCTGF) was generated using a baculoviral expression system. A human CTGF open reading frame of 1047 bp was amplified using primers engineered with BamHI sites immediately flanking the ATG start codon and TGA stop codon (forward primer 5'-GCT CCG CCC GCA GTG GGA TCC ATG ACC GCC GCC-3'; reverse primer 5'-GGA TCC GGA TCC TCA TGC CAT GTC TCC GTA-3'). A clone designated as Clone DB60R32 was used as a template, which contains the entire 2075 bp CTGF cDNA. The amplified product was subcloned into the BamHI site of PFASTBAC1 vector (Gibco/BRL), analyzed for insert orientation, and verified by sequencing of both DNA strands. Generation of recombinant baculovirus containing the CTGF cDNA was performed as outlined by Gibco/BRL (pFastBac expression system). Recombinant baculovirus stocks were isolated, expanded to high virus titer, and used to infect High Five insect cells for expression of CTGF. The recombinant CTGF was purified by heparin sepharose affinity chromatography as described previously. Peak fractions containing rhCTGF were determined by immunoblotting and Coomassie staining of sodium dodecyl sulfate (SDS)-polyacrylamide gels.

Two anti-CTGF antibodies were used. The first, anti-CTGF polyclonal designated, pAb839, was prepared by immunizing rabbits with a keyhole limpet hemocyanin-coupled synthetic peptide corresponding to amino acids 329-343 (CPG DND IFE SLY YRK) that is unique to the carboxy terminus of CTGF. The production of antibody was monitored by ELISA with the peptide conjugated to BSA and absorbed to plastic. The anti-CTGF antibodies were affinity-purified by passage through a CPG DND IFE SLY YRK-Sepharose peptide column using standard protocols (See, e.g., Harlow and Lane, 1988, *Antibodies: A Laboratory Manual*, Cold Spring Harbor Laboratory, Cold Spring Harbor N.Y.). Peptide blocking studies confirmed the monospecificity of pAb839 for CTGF in western immunoblotting assays. Western immunoblot analysis also revealed that pAb839 recognized CTGF only in a reduced conformation. The second antibody, pIgY3 polyclonal, was raised in chickens by immunizing with purified baculovirus-derived full-length rhCTGF protein, and was subsequently affinity purified through a rhCTGF-Sepharose column. (See, e.g., Kothapalli et al., 1997, *Cell Growth Differ* 8:61-68).

ELISA. The amount of specific extracellular matrix components secreted into the culture medium was quantified by ELISA, using procedures described in the art. (See, e.g., Riser et al., 1992, *J Clin Invest* 90:1932-1943.) It was previously determined in mesangial cell cultures, that media containing 0.5-1% FCS was optimal for the recovery of fibronectin and collagen. (See, e.g., Riser et al., 1992, supra.) Experimental samples of culture medium were tested in triplicate. Purified matrix components, diluted in the same medium, were run (0.5-500 ng/well) as standards. All antisera were tested for specificity before their use by immunoblotting, with and without blocking, using the extracellular matrix standards. Color intensity was measured with a TITERTEK MULTI-SCAN MCC/340 plate reader (Flow Laboratories, McLean Va., and the results analyzed using a curve-fitter computer program (Interactive Microware Inc., State College Pa.).

An indirect ELISA was used to quantitate CTGF levels in the conditioned media. Microtiter wells were coated with media samples or the rhCTGF standard (50 µl/well) for 2 hours at room temperature in a 96-well plate. The wells were washed 4 times with Dulbecco's phosphate buffered saline (D-PBS) and then incubated with pIgY3 antibody at 1.25 µg/ml (50 µl/well) in a blocking buffer of 1% BSA, 0.05% Tween 20 in D-PBS for 60 minutes. After thorough washing with D-PBS, an HRP-conjugated rabbit anti-chicken IgG (Zymed Laboratories Inc., South San Francisco Calif.) was added to all wells at a 1:6400 dilution in blocking buffer for 30 minutes. The substrate, TMB-ELISA (Gibco/BRL) was added at room temperature for 15 minutes. The reaction was stopped with 1 M sulfuric acid and the color developed measured at 450 nm in an ELISA multiscan spectrophotometer (Molecular Devices, Sunnyvale Calif.). The amount of CTGF protein present in samples was determined by using a logarithmic standard curve using serial dilutions of 3 pg to 3 ng/well of rhCTGF standard antigen.

Heparin sepharose precipitation and immunoblotting. To analyze for CTGF protein expression, conditioned media were collected and the heparin-binding proteins precipitated by end-over-end mixing for 4 hours at 4° C. with Heparin Sepharose CL-6B beads (Pharmacia, Pisctaway N.J.). The beads were washed three times with an ice cold RIPA lysis buffer comprised of 150 mM NaCl, 50 mM Tris-HCl, pH 7.5, 1% Triton X-100, 1% deoxycholate, 0.1% SDS and 2 mM EDTA. The bound proteins were then eluted by boiling in a SDS sample buffer comprised of 62 mM Tris-HCl, pH 6.8, 2.3% SDS, 10% glycerol and bromophenol blue for 5 minutes under either non-reducing, or reducing conditions containing 5% mercaptoethanol. The eluted heparin-binding proteins were resolved in 4-20% SDS-polyacrylamide gels and electrophoretically transferred to nitrocellulose filters (Schleicher and Schuell, Keene N.H.) for 2 hours at 140 mA. The filters were blocked with blocking buffer comprised of TTBS; 150 mM NaCl, 50 mM Tris, 0.2% Tween-20, 5% BSA, pH 7.4 for 2 hours at room temperature, and then probed for CTGF by incubation for 40 minutes with an anti-CTGF antibody at 0.5 µg/ml in the blocking buffer. After extensive washing at 37° C., the filters were incubated with either a HRP-conjugated donkey anti-rabbit IgG (Amersham, Arlington Heights Ill.), or a HRP-conjugated rabbit anti-chicken IgG (Zymed) at a 1:12,000 dilution in the blocking buffer. Immunoreactivity was detected by using a SUPERSIGNAL chemiluminescent substrate (Pierce, Rockford Ill.).

Additional reagents. Purified extracellular components used as standards were rat collagen I (Upstate Biotechnology Inc., Lake Placid N.Y.) and rat fibronectin (Chemicon International Inc., Temecula Calif.). The corresponding antibodies, polyclonal anti-rat collagen I and anti-rat fibronectin were used in ELISA. In preliminary experiments, the polyclonal anti-rat collagen I antibody did not cross-react with fibronectin or laminin, whereas the anti-rat fibronectin antibody did not cross-react with collagen I or laminin. The TGF-β used for stimulation experiments was human TGF-β2 (Celtrix Corporation, Santa Clara Calif.). This recombinant cytokine was produced in Chinese hamster ovary (CHO) cells and then purified by previously reported techniques (See, e.g., 1991, Ogawa et al., 1991, *Meth Enzymol* 198:317-327). A monoclonal antibody designated as 1.D 11.1, neutralizes TGF-β1, TGF-β2 and TGF-β3 (Genzyme Corporation, Cambridge Mass.).

Statistical analysis. Data was expressed as means±SEM (Standard Error Mean). For tissue culture data, unless otherwise noted, differences between two groups were evaluated using a paired Student's t-test. A paired test was utilized because of the cloned nature of the mesangial cells studied. In the case where results were normalized to corresponding control values, the data was analyzed by a one-sample t test with a hypothesized mean of 100% to compare the test group with the control. A paired two-sample t test was used to examine differences between 3 test groups. In both cases, a Holm's test was then applied post hoc to adjust for multiple comparisons. (See, e.g., Holm, 1979, *Scan J Statist* 6:65-70). For histological data, the mean sclerosis score was calculated in the glomeruli of each kidney and the statistical difference between the diabetic and control groups determined in a non-paired t-test.

A. CTGF is an Important Factor in the Pathogenesis of Renal Diseases, Including Diabetes The examples provided in the present invention, provides the first evidence demonstrating the production of CTGF protein by glomerular cells and its role as a potentially important factor in the pathogenesis of diabetic glomerulosclerosis. Hyperglycemia and glomerular hypertension are two major, well-known, casual factors of diabetic glomerulosclerosis. Prior to the present invention, the role of CTGF in the development of glomerulosclerosis has not been studied. The following examples, demonstrate that CTGF stimulates cultured mesangial cells to produce, deposit, and accumulate extracellular matrix components. The examples also demonstrate that the induction of endogenous CTGF is triggered by increased glucose concentrations, exogenous TGF-β, and mechanical strain.

As demonstrated in Example 2, CTGF mRNA is expressed in the whole kidney of normal animals, and that its level is high in comparison to the heart and brain, suggesting that endogenously produced CTGF may be involved in the normal turnover of renal extracellular matrix. However, the low levels of constitutive CTGF mRNA expression demonstrated in cultured mesangial cells suggest that this cell type may have a controlling mechanism for CTGF formation different from that in the cells forming the bulk of the renal tissue, i.e. tubular epithelial cells. The low expression of CTGF mRNA observed in mesangial cells under unstimulated conditions is associated with an apparent release of small quantities of CTGF protein into the culture medium, see Example 3. The CTGF protein was present as a 36 and 38 kD molecular species. The larger protein is equivalent in size to the full-length CTGF molecule predicted from gene analysis, whereas the smaller peptide may represent a differential N-glycosylation in the CTGF N-terminal half. It was observed that in both insect and mammalian cells, pretreatment with tunicamycin, that inhibits the N-glycosylation of glycoproteins, the larger CTGF band is reduced in its migration to localize with the smaller moiety. These molecular species observed in mesangial cells are similar in size to that secreted by vascular endothelial and fibroblast cells (See, e.g., Bradham et al., 1991, supra; Kothapalli et al., 1997, supra; and Steffen et al., 1998, *Growth Factors* 15:199-213.) The small amounts of CTGF detected in the conditioned medium of mesangial cultures were not the result of low levels of its synthesis, but were rather due to the restricted release of the protein into medium. This was indicated by the ability of sodium-heparin to dramatically increase the levels of CTGF protein measured in the media. (See Example 3.) These results suggest that as much as 80% of the CTGF synthesized by mesangial cells remains cell- or matrix-bound. In a quantitative assay it is shown that, in the presence heparin, mesangial cells secrete approximately 7 ng of CTGF per $10^6$ cells in each 24 hour period. (See Example 3.)

Given that CTGF stimulates extracellular matrix accumulation, it was examined whether known factors implicated in the development of diabetic glomerulopathy alter CTGF mRNA expression. High extracellular glucose concentrations markedly increased the levels of CTGF mRNA as well as the production of CTGF protein in mesangial cells. (See, Example 4.) In a similar manner, TGF-β also upregulates the expression of CTGF mRNA and protein. With strong upregulation, as occurred in response to TGF-β, there was a marked induction of a small molecular weight CTGF species, which according to its size of ~18 kD, is approximately half of the full-length CTGF molecule. (See, Example 2 and FIG. 6.) The size and properties of this small molecular weight CTGF species recovered from a heparin-sepharose column indicated that it contains both the thrombospondin 1 and the C-terminal modules of CTGF. The small molecular species demonstrated in mesangial cells following stimulation, may have distinct biological activities as compared to the whole molecule. Since TGF-β secretion in mesangial cells is stimulated by increased ambient glucose concentrations, the observed induction of CTGF by high glucose may occur indirectly, mediated by the action of TGF-β. The neutralization studies described in Example 5 demonstrated a direct role for the cytokine in the process, since incubation with TGF-β antibodies resulted in a complete blockade of CTGF stimulation. (See FIG. 8.)

Cyclic mechanical strain was also examined as a possible regulatory element in CTGF expression. The results demonstrated that stretching is a potent stimulus for the upregulation of CTGF mRNA levels (See Example 7 and FIG. 10). The rapid induction of CTGF mRNA following stretch suggests that TGF-β production and/or activity may not be required to mediate the initial effects of mechanical strain. Cyclic strain induces TGF-β1 synthesis and activation, but this effect is only evident after 48-72 hours of mechanical stimulation. (See, e.g., Riser et al., 1992, supra). These studies also demonstrated that TGF-β and CTGF are able to autoinduce their own expression in mesangial cells. (See, Example 3 and FIG. 3.) This autoinducing action of CTGF is the first time that such action has been observed for CTGF. Furthermore, this action appears to be selective, since exogenous CTGF has no effect on TGF-β transcript levels. (See, FIG. 3.) These findings suggested that once stimulated by TGF-β, CTGF mRNA levels in mesangial cells may remain elevated even in the absence of additional TGF-β activity resulting in a continued enhancement of extracellular matrix synthesis and deposition, which may explain the prevalent inability to totally block extracellular matrix production in mesangial cells and in the mesangium by TGF-β neutralization. (See, e.g., Border et al., 1990, supra; Sharma et al., 1996, supra; and Ziyadeh et al., 1994, supra.)

Quantitative glomerular expression of CTGF mRNA in db/db mice (See, Example 10), demonstrated that CTGF action is a factor in the initiation of glomerular extracellular matrix deposition in diabetes. While CTGF mRNA is expressed in normal glomeruli, the levels are dramatically upregulated by 28-fold, after a short period of diabetes and before the onset of overt glomerular disease (See Example 10). As demonstrated in these examples, CTGF mRNA upregulation occurred at a time when glomerular fibronectin mRNA levels were increased. However, the glomerular mesangial expansion was minimal and proteinuria insignificant. As compared to glomeruli, the much lower upregulation of CTGF observed in the whole kidney as demonstrated in Example 10 shows that the CTGF is, at least in the early phases of nephropathy, primarily involved in the induction of the glomerular alterations. However, in the more advanced stages of diabetic nephropathy, CTGF may be an important inducer of tubulointerstitial disease.

In summary, the following examples essentially demonstrate that, in addition to enhanced glomerular TGF-β expression, CTGF upregulation is an important factor in the excess deposition of the extracellular matrix by mesangial cells. This CTGF upregulation is driven by a combination of high glucose concentrations and cellular mechanical stain via pathways that are both dependent and independent of TGF-β stimulation.

B. Experimental Data Demonstrating Nexus Between the Presence of CTGF and the Onset and Progression of Renal Disorders, Including Diabetes Example 1

CTGF-Induced Changes In Extracellular Matrix Production Of Mesangial Cells. To determine the effects of exogenous CTGF on mesangial cell production of the extracellular matrix, serum-depleted cells were exposed for 48 hours to media containing 20 ng/ml of rhCTGF. For comparison purposes, additional cultures were incubated in media without exogenous CTGF, but containing either 2 ng/ml of TGF-β, or 20 mM glucose. As anticipated, exogenous TGF-β and the high glucose concentration increased the amount of secreted fibronectin by 23 and 30%, respectively, over that of controls as shown in FIG. 1A. The presence of exogenous CTGF in the media also effectively stimulated fibronectin secretion by 45%. Like fibronectin, the quantity of secreted collagen type I was also increased by 64% CTGF, as well as by 50% TGF-β or 22% high glucose as shown in FIG. 1B.

Example 2

Renal And Mesangial Cell CTGF Expression: Regulation By TGF-β. It was determined whether cultured rat mesangial cells expressed CTGF mRNA, and the results were compared to those from whole kidney. Northern analysis demonstrated a single 2.4 kb CTGF transcript in mesangial cells and whole kidney, but in contrast no detectable message was evident in cultured kidney fibroblasts as demonstrated in FIG. 2. When compared to other tissues, the most abundant expression was in the kidney, being approximately 20-fold higher than in the brain.

To determine if TGF-β was a regulatory factor in mesangial cell expression of CTGF message, cells were serum-depleted, exposed to 2 ng/ml of TGF-β for 24 hours, the mRNA was then probed. Changes in TGF-β transcript levels were also monitored. Exogenous TGF-β exposure increased the expression of CTGF mRNA greater than 4-fold as shown in FIG. 3A and FIG. 3B, whereas TGF-β mRNA increased 80% (see FIG. 3A and FIG. 3C). To determine whether CTGF was capable of regulating its own expression, or that of TGF-β, mesangial cells were also exposed to 20 ng/ml of rhCTGF. As shown in FIG. 3A and FIG. 3C, this treatment did not alter the level of TGF-β mRNA, but in contrast, strongly autoinduced CTGF message as demonstrated in FIG. 3A and FIG. 3B.

To demonstrate whether low CTGF mRNA expression in unstimulated mesangial cells was associated with a detectable production of the corresponding protein, and to determine the effects of TGF-β, cells were serum depleted and then cultured for an additional 24 hours in fresh maintenance medium in the presence or absence of 2 ng/ml exogenous TGF-β. The conditioned medium was subsequently heparin-sulfate precipitated and analyzed by immunoblotting using two different anti-CTGF antibodies. Immunoblotting with pIgY3 antibody, raised against the full-length rhCTGF, demonstrated that under basal, unstimulated conditions mesangial cells secreted very small amounts of CTGF (see FIG. 4A). However, upon exposure to TGF-β, the secretion of CTGF protein was markedly stimulated. The predominant product detected in these cultures migrated to the same position as the recombinant standard. Immunoblotting of the same samples with the pAb839 antibody, raised against a 15 amino acid sequence unique to CTGF, confirmed the identity of the protein detected (see FIG. 4B).

Example 3

Detection Of CTGF In Mesangial Cells. The CTGF protein detected in mesangial cell cultures above represents free molecules present in the media. The existence of a heparin binding domain within CTGF suggests that a substantial portion of the synthesized and released protein exists bound to proteoglycans, or to fibronectin, present on the cell surface or in the extracellular matrix. To ascertain whether this was the case, and to determine the time course for appearance of CTGF in the extracellular environment under unstimulated conditions, mesangial cell cultures were serum-deprived and then fresh maintenance media containing 50 μg/ml of sodium heparin was added. Conditioned media were collected after defined incubation periods and the majority of the sample pooled and heparin-sulfate precipitated. Immunoblotting of the 4 hour samples produced faint CTGF bands at approximately 36 and 39 kD (see, FIG. 5A). The intensities of these bands increased sharply by 24 hours and remained elevated throughout the 72 hour incubation period. At 48 and 72 hours, when the full-length CTGF bands were intense, a faint additional band with an electrophoretic mobility of approximately 20 kD could also be detected. As previously demonstrated, in the absence of sodium heparin, the CTGF present in the media was barely detectable, suggesting that the majority of CTGF protein produced was bound to the cell and/or substrate. Because immunoblotting is largely a qualitative assay, individual supernatants were also evaluated by ELISA prior to their pooling and precipitation, and the results were expressed on a per cell basis. This highly quantitative assay demonstrated a time dependent increase in CTGF, with approximately 7 ng/$10^6$ cells being secreted in a 24-hour period as shown in FIG. 5B. The amount of CTGF secreted in the medium during the total 72-hour period was reduced to 20% in the absence of heparin.

In a subsequent experiment, the regulation of secreted CTGF by TGF-β was reexamined, in the presence of heparin. Accordingly, mesangial cells were serum-deprived, then incubated for 48 hours in a maintenance media containing 50 μg/ml of sodium heparin and 2 ng/ml TGF-β. Immunoblotting of pooled, precipitated media samples indicated that TGF-β markedly increased the secretion of full-length (36-39 kDa) CTGF as demonstrated in FIG. 6A. However, even more pronounced was the induction of the molecule(s) appearing at 18-20 kDa. This smaller moiety corresponds in size to half of the full-length CTGF molecule. Quantitative analysis by ELISA of the individual samples, prior to being pooled and precipitated for immunoblotting, demonstrated a 2.5-fold enhancement of total secreted CTGF in response to TGF-β treatment (see FIG. 6B).

Example 4

Mesangial Cell Expression Of CTGF: Regulation By Glucose Concentrations. To determine if CTGF expression might also be altered by the ambient concentration of glucose, mesangial cell cultures continuously grown in 5 mM glucose were incubated for 14 days in growth media containing 35 mM glucose. The time was chosen because previous studies demonstrated that this period was required for the full induction of ECM protein production. (See, e.g., Pugliese et al., 1997, *J Am Soc Nephrol* 8(3):406-414.) As shown in FIG. 7, mesangial cells grown in medium containing 5 mM glucose concentration demonstrated minimal levels of CTGF message. However, following long-term exposure to an increased glucose concentration, mesangial cell transcripts for CTGF were markedly upregulated, reaching a 7-fold level above control, as determined by quantitative image analysis as depicted in FIG. 7.

To examine the effects of high glucose exposure on the secretion of CTGF protein, serum-deprived cultures that shortened the exposure time to 48 hours, and included sodium heparin in the medium were used. This protocol allowed a comparison to the effects of TGF-β. Immunoblotting of pooled and precipitated media samples indicated that exposure to 20 mM of glucose increased the amount of CTGF secreted as shown in FIG. 6A. Interestingly, however, this stimulation appeared to be limited to the full-length molecule only. Quantitation of secreted CTGF protein by ELISA, prior to pooling and precipitation demonstrated a 2-fold induction by high extracellular glucose levels as demonstrated in FIG. 6B, which is an increase similar to that induced by TGF-β, under the experimental conditions selected. To determine if the observed increase in CTGF could be due to an osmolar effect, the experiments were repeated using a mannitol. Under these conditions, there was no induction of CTGF released as measured by ELISA (5 mM glucose, 2.39±0.28 ng/$10^6$ cells; 5 mM glucose plus 15 mM mannitol, 1.94±0.32), and no change in the distribution of CTGF forms secreted as determined by immunoblotting.

Example 5

TGF-β Block Of High Glucose-Induced CTGF Production. To determine if TGF-β is responsible for CTGF production by mesangial cells in the presence of high glucose, mesangial cells were cultured for 14 days in the presence of either 5 mM glucose or 20 mM glucose, and were seeded and grown under the same glucose conditions for an additional 8 day period. On day 4, the cultures were serum-deprived, and half received 20 μg/ml of an antibody that neutralizes TGF-β1, 2 and 3 activity. Fresh antibody was added daily, and the media was replaced 24 hours prior to collection. Measurement of CTGF secretion by ELISA demonstrated a stimulatory effect of high glucose as depicted in FIG. 8. However, neutralization of TGF-β activity in these cultures blocked the induction of CTGF by high glucose. While the constitutive secretion of CTGF in the presence of normal concentrations of glucose also appeared somewhat reduced by the presence of a TGF-β antibody, this change was not statistically significant (p=0.09). Also non-significant (p=0.075) was the difference in CTGF levels in normal glucose- and high glucose-treated cells when TGF-β was neutralized (see FIG. 8).

Example 6

Glucose transporter expression and CTGF production. Mesangial cells transduced with the human glucose transporter 1 (GLUT1) gene producing a line designated, MCGT1, demonstrated a 10-fold increase in GLUT1 protein, a 5-fold increase in glucose uptake and a 2-3 fold increase in the synthesis of collagen types I and IV, fibronectin and laminin, as compared to a control mesangial cell line, designated MCLacZ, and transduced with the bacterial β-galactosidase gene. These cell lines were used to demonstrate that the increase in intracellular glucose, rather than simply the extracellular glucose concentration per se, is the major determinant of exaggerated extracellular matrix formation by mesangial cells in culture. (See, e.g., Helig et al., 1995, supra.) To determine if CTGF is also increased in this in vitro model of diabetes, MCCT1 and MCLacZ cells were seeded and grown for 48 hours in RPMI with 20% NuSerum, 8 mM glucose. Cells were then washed twice in serum-free media and fresh RPMI containing 1% FCS added. Conditioned media were collected 24 hours later and CTGF protein levels were determined by ELISA. Approximately 80 ng of CTGF/$10^6$ cells was detected in the media of the control MCLacZ cultures whereas the level nearly doubled (147 ng/$10^6$ cells) in MCGT1 cultures as shown in FIG. 9.

Example 7

Mesangial Cell Expression Of CTGF: Regulation By Cyclic Mechanical Strain. To determine if cyclic mechanical strain was also a factor capable of altering mesangial cell expression of CTGF, cells were seeded into collagen-coated flexible-bottom plates, then after overnight incubation, and subjected to either stretch or maintained under static conditions. Stretching was set at 3 cycles per minute and 19% maximum elongation using the computer-controlled system previously described in Riser et al., 1992, supra, and Riser et al., 1996, supra. This degree of stretching was chosen to approximate the mechanical force experienced by mesangial cells in vivo. (See, e.g., Cartes et al., 1997, supra.)

At the designated periods, the cells were lysed and total RNAs extracted and probed for CTGF transcripts. Cyclic stretching induced a rapid and marked increase in CTGF message as shown in FIG. 9. Quantitative image analysis of the Northern blot showed that levels of CTGF mRNA increased more than 2-fold by 4 hours and remained elevated at this level after 8 hours of stretching. Additional experiments demonstrated that CTGF transcripts were significantly increased even after 48 hours of stretch.

Example 8

Blockade Of Stimulated Collagen Production By Anti-CTGF Antibody. Mesangial cells were grown for 4 days in RPMI medium with 20% NU-SERUM media supplement (Collaborative Research), the medium was replaced with one containing 1% FCS (serum-deprived conditions) and 0 or 5 ng/ml of TGF-β2. Half of the cultures received anti-CTGF antibody (goat affinity purified, pGAP) and the other half received non-immune goat IgG. Fresh antibody was added daily, and the media was replaced 24 hours prior to collection. Media from individual wells were tested by ELISA. As shown in FIG. 11, treatment with anti-CTGF antibody did not alter the production of baseline collagen, but completely blocked the increased production due to TGF-β. There was no significant difference between the amount of collagen produced in unstimulated cultures as compared to that of cultures stimulated by TGF-β, but treated by anti-CTGF antibody.

Example 9

Blockade Of Stimulated Mesangial Cell Proliferation By Anti-CTGF Antibody. Mesangial cells were grown for four days in RPMI medium with 20% NU-SERUM media supplement (Collaborative Research), the medium was replaced with one containing 1% FCS (serum-deprived conditions) and 0 or 5 ng/ml of TGF-β2. Half of the cultures received anti-CTGF antibody (goat affinity purified, pGAP) and the other half non-immune goat IgG. Fresh antibody was added daily, and the media was replaced 24 hours prior to collection. Media from individual wells were tested by ELISA. As shown in FIG. 12, TGF-β treatment significantly induced (87%) mesangial cell proliferation. Treatment with anti-CTGF antibody significantly reduced (approximately 50%), the induction of cell proliferation. The same antibody treatment had no effect on basal proliferation, i.e., under unstimulated conditions.

Example 10

CTGF Expression In Experimental Diabetic Nephropathy. To Determine if CTGF is upregulated in early diabetic nephropathy, studies were carried out on diabetic db/db mice, and the results compared to those from age-matched nondiabetic db/m littermates. At 5 months of age, approximately 3.5 months after the onset of diabetes, animals were evaluated for blood glucose levels, total weight, proteinuria, and mesangial expansion. At the time of sacrifice, mean blood glucose levels, as well as body weights, were significantly greater in the db/db animals as shown in the following Table 1.

TABLE 1

|  | Control db/m | Diabetic db/db |  |
| --- | --- | --- | --- |
| Blood Glucose | 142 ± 19.0 mg/dL, n = 8 | 485 ± 58.0, n = 6 | P < 0.001 |
| Weight | 29.2 ± 1.00 g, n = 8 | 43.1 ± 7.30, n = 6 | P < 0.001 |
| Proteinuria | 2.32 ± 1.07 mg/24 h, n = 10 | 2.78 ± 0.93, n = 9 | P = 0.330 |
| Glomerular Sclerosis | 0.101 ± 0.048, n = 17 | 0.649 ± 0.369, n = 6 | P = 0.003 |

As shown in FIG. 13, inspection of the renal tissue by light microscopy demonstrated that the diabetic animals exhibited noticeable, but minimal, glomerular changes consistent with early diabetic glomerulosclerosis, i.e. mild mesangial matrix expansion without apparent tubulointerstitial disease. In addition, Table 1 shows that the level of proteinuria was not significantly greater than in controls. Semiquantitative analysis of the glomerular changes demonstrated that the observed mesangial expansion in the diabetic animals was indeed consistent, but of mild intensity. A value of zero (0) represents no lesion and a value of one (1) represents minimal mesangial expansion in the majority of glomeruli, without basement membrane thickening.

Northern analysis of whole kidney RNAs indicated that the CTGF message levels were markedly increased in 4 out of 5 diabetic mice as shown in FIG. 14A. These changes were mirrored by parallel changes in fibronectin transcript levels. Quantitation of results yielded a mean 103% increase in CTGF expression while fibronectin levels were 80% greater than in the controls as shown in FIG. 14B and FIG. 14C. Moreover, transcript levels were detected in competitive RT-PCR for CTGF mRNA in a single sample from diabetic mouse glomeruli as compared to the control GAPDH sample as depicted in FIG. 15A and FIG. 15B. Analysis of microdissected glomeruli identified multiple animals (5 diabetic and 5 control groups), that by a competitive and quantitative RT-PCR method (described above), identified a low, but measurable, transcript level of CTGF in the glomeruli of control animals. (See FIG. 16.) In mice with diabetes, the level of CTGF was dramatically increased by 27-fold. (See FIG. 16.) The upregulation of glomerular CTGF mRNA was accompanied by a nearly 5-fold increase in the amount of fibronectin mRNA. These large differences were not due to dissimilar glomerular size resulting from diabetic hypertrophy, since the level of GAPDH message was not significantly increased in diabetic animals as compared to controls (control, $1.39 \pm 0.524 \times 10^{-1}$ attomoles/glomerulus; diabetic $2.59 \pm 0.307$; P>0.05). Therefore, a dramatic increase in CTGF expression was documented at a time when changes in the kidney were minimal.

C. Detection of CTGF in Samples as an Indicator of Renal Diabetes Associated Disorders Example 11

The Presence And Stability Of Urinary CTGF. To Examine Whether CTGF protein was secreted in the urine, and to examine the stability of the CTGF molecule after its secretion in the urine, samples of urine were collected from a healthy donor and divided into five, 25-ml aliquots. Various amounts of rhCTGF, ranging from 25 to 750 ng, were added to four of the five aliquots (the "spiked samples"). The fifth aliquot served as a control, receiving no added CTGF (the "unspiked sample). All samples were frozen, and stored at −70° C., then later thawed and clarified by centrifugation. Following heparin sepharose quantitative extraction of samples, immunoblotting was performed using CTGF specific antibody as indicated in FIG. 17. The results identified the presence of a scarcely detectable level of CTGF secretion in the urine of the unspiked sample. Further, the stability of the CTGF protein in the urine was demonstrated by the progressive increase in CTGF recovered in the spiked samples. Comparison of sample lanes with that containing freshly added rhCTGF (35 ng) indicated that CTGF was largely, if not entirely, preserved.

Example 12

CTGF In The Urine Of Renal Patients. The quantity and/or molecular form of CTGF present in the urine that might be altered in patients with established nephropathy, including that associated with diabetes, was investigated. Urine samples from 8 ambulatory patients being treated for a variety of kidney diseases, of which 3 had a history of diabetes, were collected and frozen during routine visits (Nephrology and Hypertension Clinic, Henry Ford Hospital). Similarly, samples were also obtained from 3 normal healthy volunteers with no history of kidney disease. All samples were later batch-thawed and processed above. CTGF was detected in 1 of 3 normal volunteers, and in all patient samples as shown in FIG. 18. Immunoreactive CTGF appeared in 3 different molecular forms. A CTGF band (doublet) was present in 1 control sample and 4 of 8 patients samples. Interestingly, a large molecular weight band, approximately 200 kDA, was present in every patient sample, appearing only as a very faint band in a single control sample. This large band likely represents CTGF in complex with a second, unknown urinary protein. Even more intriguing was a unique small CTGF fragment, approximately 9-12 kDa. This smaller moiety appears to be equivalent to the heparin binding C-terminal quarter fragment of CTGF, and was present in the urine of all 3 diabetic patients, but not present in nondiabetic patients or healthy controls. Interestingly, this product may compare to the CTGF fragment produced by mesangial cells in culture when stimulated by high glucose concentrations of TGF-β.

In a separate experiment, CTGF in human urine samples was measure by ELISA, and presented in the following Table 2.

TABLE 2

| | Patient Population | | |
|---|---|---|---|
| Patient Number | Healthy Control | Kidney Disease | Diabetic: No Kidney Disease |
| 1 | 0.81 | 0.36 | 0.68 |
| 2 | 0.43 | 1.22 | 7.12 |
| 3 | 0.84 | 5.46 | 5.68 |
| 4 | 0.67 | 2.53 | 0.40 |
| 5 | | 5.72 | 0.56 |
| 6 | | 0.78 | 3.84 |
| 7 | | 3.47 | |
| Mean CTGF | 0.69 | 2.79 | 3.05 |
| ±SE | 0.10 | 0.83 | 1.12 |

Table 2 compares the amounts of CTGF detected in healthy volunteers to patients with kidney disease (in some cases associated with diabetes), or to patients with 5 to 10 years with diabetes, but without kidney disease. Each group had 4 to 7 samples from different individuals. Amounts of CTGF/ml were first determined by ELISA, comparing sample values to a standard curve using serial dilutions of a known quantity of rhCTGF. To standardize results (i.e. to account for variation in the production of urine), amounts of CTGF (CTGF/ml) were then divided by the urine creatinine from the same patient, determined from the same urine.

The results demonstrate that healthy individuals demonstrate consistently low levels of urinary CTGF. However, among those with kidney disease the mean level of CTGF increased 4-fold. In those patients with diabetes, but as yet undiagnosed kidney disease, there was a similar 4.4-fold increase. It was expected that because only approximately 40% of those with diabetes will go on to develop nephropathy, a similar percent of patients would exhibit increased CTGF levels. Interestingly, of the 6 diabetic patients tested, 3, or 50%, demonstrated clearly elevated CTGF levels. The remaining patients appeared to have values similar to those of the healthy volunteers.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims. All patents, publications, and other references cited herein are incorporated by reference herein in their entirety.

What is claimed is:

1. A method for diagnosing the presence of a renal disorder in a subject having diabetes, the method comprising:
   (a) obtaining a urine sample from the subject;
   (b) contacting the urine sample with an antibody specific to CTGF under conditions suitable for the antibody to bind to CTGF;
   (c) detecting the level of antibody bound to CTGF, wherein the level of CTGF in the urine sample is determined by detecting the level of antibody bound to CTGF; and
   (d) comparing the level of CTGF in the urine sample to a standard level of CTGF, wherein the standard level of CTGF is from the urine of a normal population or from a diabetic patient population without a renal disorder and wherein an increased level of CTGF is indicative of the presence of a renal disorder.

2. The method of claim 1, wherein the renal disorder is diabetic nephropathy.

3. A method for detecting the presence of a renal disorder in a subject having diabetes, the method comprising:
   (a) obtaining a urine sample from the subject;
   (b) contacting the urine sample with an antibody specific to CTGF under conditions suitable for the antibody to bind to CTGF;
   (c) detecting the level of antibody bound to CTGF, wherein the level of CTGF in the urine sample is determined by detecting the level of antibody bound to CTGF; and
   (d) comparing the level of CTGF in the urine sample to a standard level of CTGF, wherein the standard level of CTGF is from the urine of a normal population or from a diabetic patient population without a renal disorder and wherein an increased level of CTGF is indicative of the presence of a renal disorder.

4. The method of claim 3, wherein the renal disorder is diabetic nephropathy.

5. A method for identifying a predisposition or susceptibility to a renal disorder in a subject having diabetes, the method comprising:
(a) obtaining a urine sample from the subject;
(b) contacting the urine sample with an antibody specific to CTGF under conditions suitable for the antibody to bind to CTGF;
(c) detecting the level of antibody bound to CTGF, wherein the level of CTGF in the urine sample is determined by detecting the level of antibody bound to CTGF; and
(d) comparing the level of CTGF in the urine sample to a standard level of CTGF, wherein the standard level of CTGF is from the urine of a normal population or from a diabetic patient population without a renal disorder and wherein an increased level of CTGF is indicative of the predisposition or susceptibility to a renal disorder.

* * * * *

SEQUENCE LISTING

<160> NUMBER OF SEQ ID NOS: 7

<210> SEQ ID NO 1
<211> LENGTH: 25
<212> TYPE: DNA
<213> ORGANISM: Homo sapiens

<400> SEQUENCE: 1
gagtgggtgt gtgacgagcc caagg                                       25

```
-continued

<210> SEQ ID NO 2
<211> LENGTH: 25
<212> TYPE: DNA
<213> ORGANISM: Homo sapiens

<400> SEQUENCE: 2
atgtctccgt acatcttcct gtagt                                          25

<210> SEQ ID NO 3
<211> LENGTH: 20
<212> TYPE: DNA
<213> ORGANISM: Rattus norvegicus

<400> SEQUENCE: 3
tgccactgtt ctcctacgtg                                                20

<210> SEQ ID NO 4
<211> LENGTH: 20
<212> TYPE: DNA
<213> ORGANISM: Rattus norvegicus

<400> SEQUENCE: 4
atgctttgac ccttacacgg                                                20

<210> SEQ ID NO 5
<211> LENGTH: 33
<212> TYPE: DNA
<213> ORGANISM: Homo sapiens

<400> SEQUENCE: 5
gctccgcccg cagtgggatc catgaccgcc gcc                                 33

<210> SEQ ID NO 6
<211> LENGTH: 30
<212> TYPE: DNA
<213> ORGANISM: Homo sapiens

<400> SEQUENCE: 6
ggatccggat cctcatgcca tgtctccgta                                     30

<210> SEQ ID NO 7
<211> LENGTH: 15
<212> TYPE: PRT
<213> ORGANISM: Homo sapiens

<400> SEQUENCE: 7

Cys Pro Gly Asp Asn Asp Ile Phe Glu Ser Leu Tyr Tyr Arg Lys
1               5                   10                  15
```